（12） United States Patent
Shelton, IV et al.

(10) Patent No.: US 9,848,876 B2
(45) Date of Patent: Dec. 26, 2017

(54) DEVICES AND METHODS FOR FACILITATING EJECTION OF SURGICAL FASTENERS FROM CARTRIDGES

(71) Applicant: Ethicon Endo-Surgery, Inc., Cincinnati, OH (US)

(72) Inventors: Frederick E. Shelton, IV, Hillsboro, OH (US); Emily A. Schellin, Cincinnati, OH (US); Brian F. Dinardo, Cincinnati, OH (US); Adam R. Dunki-Jacobs, Cincinnati, OH (US); Charles J. Scheib, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 482 days.

(21) Appl. No.: 14/474,713

(22) Filed: Sep. 2, 2014

(65) Prior Publication Data

US 2016/0058446 A1     Mar. 3, 2016

(51) Int. Cl.
| | |
|---|---|
| *A61B 17/068* | (2006.01) |
| *A61B 17/072* | (2006.01) |
| *A61B 17/064* | (2006.01) |
| *A61B 17/29* | (2006.01) |
| *A61B 17/00* | (2006.01) |
| *A61B 90/00* | (2016.01) |

(52) U.S. Cl.
CPC .... *A61B 17/07207* (2013.01); *A61B 17/0644* (2013.01); *A61B 2017/00526* (2013.01); *A61B 2017/07271* (2013.01); *A61B 2017/07278* (2013.01); *A61B 2017/07285* (2013.01); *A61B 2017/2933* (2013.01); *A61B 2017/2936* (2013.01); *A61B 2090/037* (2016.02)

(58) Field of Classification Search
CPC ............ A61B 17/07207; A61B 17/068; A61B 2017/07278; A61B 2017/2933; A61B 17/0644; A61B 2090/037
USPC ........................................... 227/175.1, 176.1
See application file for complete search history.

(56) References Cited

U.S. PATENT DOCUMENTS

| | | | | |
|---|---|---|---|---|
| 4,608,981 | A | * | 9/1986 | Rothfuss .......... A61B 17/07207 227/180.1 |
| 5,465,895 | A | | 11/1995 | Knodel et al. |
| 5,725,536 | A | | 3/1998 | Oberlin et al. |

(Continued)

FOREIGN PATENT DOCUMENTS

WO    WO-2009033057 A2    3/2009

OTHER PUBLICATIONS

"MicroCutter XCHANGE™ 30." Inservice Poster. (Oct. 2013).

(Continued)

*Primary Examiner* — Michelle Lopez
(74) *Attorney, Agent, or Firm* — Mintz Levin Cohn Ferris Glovsky and Popeo, P.C.

(57) ABSTRACT

Devices and methods are provided for facilitating ejection of surgical fasteners from a cartridge. In general, the devices and methods can facilitate complete removal of one or more fasteners from within the cartridge. In an exemplary embodiment, a surgical device can be configured to facilitate disconnection of fasteners from a carrier to which the fasteners are frangibly attached. The surgical device can include a separation feature in the form of a shearing element configured to facilitate separation of the fasteners from the carrier when the fasteners are deployed from a cartridge that has the fasteners and the carrier disposed therein.

13 Claims, 17 Drawing Sheets

(56) References Cited

U.S. PATENT DOCUMENTS

| | | |
|---|---|---|
| 7,000,818 B2 | 2/2006 | Shelton, IV et al. |
| 7,473,258 B2 | 1/2009 | Clauson et al. |
| 7,533,790 B1 | 5/2009 | Knodel et al. |
| 7,641,671 B2 | 1/2010 | Crainich |
| 7,669,746 B2 | 3/2010 | Shelton, IV |
| 7,678,121 B1 | 3/2010 | Knodel |
| 7,753,250 B2 | 7/2010 | Clauson et al. |
| 7,918,376 B1 | 4/2011 | Knodel et al. |
| 7,954,683 B1 | 6/2011 | Knodel et al. |
| 7,963,432 B2 | 6/2011 | Knodel et al. |
| 7,988,026 B2 | 8/2011 | Knodel et al. |
| 8,056,789 B1 | 11/2011 | White et al. |
| 8,066,720 B2 | 11/2011 | Knodel et al. |
| 8,070,034 B1 | 12/2011 | Knodel |
| 8,070,036 B1 | 12/2011 | Knodel |
| 8,087,562 B1 | 1/2012 | Manoux et al. |
| 8,123,795 B1 | 2/2012 | Knodel et al. |
| 8,261,958 B1 | 9/2012 | Knodel |
| 8,272,551 B2 | 9/2012 | Knodel et al. |
| 8,317,071 B1 | 11/2012 | Knodel |
| 8,317,072 B1 | 11/2012 | Knodel et al. |
| 8,356,740 B1 | 1/2013 | Knodel |
| 8,357,174 B2 | 1/2013 | Roth et al. |
| 8,365,973 B1 | 2/2013 | White et al. |
| 8,403,956 B1 | 3/2013 | Thompson et al. |
| 8,439,245 B2 | 5/2013 | Knodel et al. |
| 8,439,246 B1 | 5/2013 | Knodel |
| 8,496,155 B2 | 7/2013 | Knodel |
| 8,505,800 B1 | 8/2013 | Knodel et al. |
| 8,556,153 B1 | 10/2013 | Knodel |
| 8,631,992 B1 | 1/2014 | Hausen et al. |
| 8,636,189 B1 | 1/2014 | Knodel et al. |
| 8,679,155 B2 | 3/2014 | Knodel et al. |
| 8,701,960 B1 | 4/2014 | Manoux et al. |
| 9,004,339 B1 | 4/2015 | Park |
| 2009/0065552 A1* | 3/2009 | Knodel ............... A61B 17/072 227/180.1 |
| 2010/0155453 A1 | 6/2010 | Bombard et al. |
| 2011/0204120 A1 | 8/2011 | Crainich |
| 2012/0010652 A1 | 1/2012 | Hahnen et al. |
| 2013/0233908 A1 | 9/2013 | Knodel et al. |
| 2013/0277410 A1 | 10/2013 | Fernandez et al. |
| 2014/0041191 A1 | 2/2014 | Knodel |
| 2014/0175146 A1 | 6/2014 | Knodel |

OTHER PUBLICATIONS

"MicroCutter XCHANGE™ 30." Instructions for Use. (2014).
"MicroCutter XCHANGE® 30 Videos." Cardica. Web. May 7, 2014. http://www.cardica.com/inservice-guide.php.
"MicroCutter XCHANGE® 30: The World's First and Only Articulating 5mm Stapler." Cardica. Web. May 7, 2014. http://www.cardica.com/minimally-invasive-surgery.php.
U.S. Appl. No. 14/300,954, filed Jun. 10, 2014.
European Search Report for Application No. EP 15183377.9, dated May 3, 2016.

* cited by examiner

DEVICES AND METHODS FOR FACILITATING EJECTION OF SURGICAL FASTENERS FROM CARTRIDGES

FIELD OF THE INVENTION

The present disclosure relates generally to facilitating ejection of surgical fasteners from cartridges.

BACKGROUND

Minimally invasive surgical instruments are often preferred over traditional open surgical devices due to the reduced post-operative recovery time and minimal scarring associated with minimally invasive procedures. Laparoscopic surgery is one type of minimally invasive surgery (MIS) procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. Endoscopic surgery is another type of MIS procedure in which elongate flexible shafts are introduced into the body through a natural orifice.

Due to the benefits associated with minimally invasive surgeries, significant efforts have gone into developing a range of endoscopic and laparoscopic surgical instruments that are suitable for precise placement of a distal end effector at a desired surgical site. These distal end effectors engage the tissue in a number of ways to achieve a diagnostic or therapeutic effect (e.g., grasper, cutter, stapler, clip applier, access device, drug/gene therapy delivery device, and energy device using ultrasound, radiofrequency, laser, etc.).

For example, staplers including end effectors for grasping tissue have been developed which secure tissue between two jaws. Staples contained in one of the jaws can be driven into the grasped tissue and deformed to hold the tissue by impinging on the other jaw. The staples can form a predetermined pattern (e.g., one or more lines of staples) based upon the configuration of the staples in the one of the jaws. The stapler can be a linear stapler, in which the predetermined pattern includes one or more longitudinal lines of staples. Though staplers can be effective to grasp and staple tissue, it can be difficult to grasp and/or staple the tissue based on a variety of factors, such as a size and/or shape of the staple, a thickness and/or toughness of the tissue, etc.

Some staplers can be refilled after firing staples. In some staplers, the staples can be contained in a cartridge which can be removable from the stapler's jaw to allow the stapler to be refilled with staples contained in another cartridge inserted into the jaw. However, this refilling of cartridges can be difficult since the cartridges can be relatively small and accordingly difficult to manipulate and/or properly secure within the jaw. Refilling a stapler with a new cartridge can thus be time consuming and/or can result in an improperly loaded cartridge that can misfire staples or otherwise function improperly during use on a patient.

Accordingly, there remains a need for improved methods and devices for stapling tissue.

SUMMARY

A surgical fastening device for treating tissue comprises an elongate shaft, an end effector coupled to a distal end of the elongate shaft, a plurality of fasteners disposed within the jaw and frangibly coupled to a carrier, a sled configured to advance distally through the jaw to cause each of the plurality of fasteners to rotate into tissue engaged between the jaw and the anvil, and a shearing element slidably moveable within the jaw to shear each fastener from the carrier, wherein the shearing element is separate from the sled such that the shearing element is configured to shear the fasteners from the carrier after the fasteners are driven into tissue by the sled. The end effector includes a jaw and an anvil pivotally connected to the jaw, the jaw and the anvil being configured to engage tissue therebetween. In one aspect the shearing element is positioned proximal of the sled. In another aspect the shearing element is coupled to a distal end of the sled. In one aspect the shearing element includes a plurality of upright wedges configured to shear the fasteners from the carrier.

In one aspect the fastening device further comprises an I-beam positioned proximal of the shearing element and configured to be slidably received within the anvil and the jaw. In another aspect the sled includes a plurality of wedges configured to contact and drive the fasteners into tissue, and a knife for cutting tissue engaged between the jaw and the anvil, and wherein the shearing element is positioned proximal of the wedges and the knife. The shearing element is configured such that it shears the fasteners from the carrier during proximal movement of the shearing element through the jaw. In one aspect the shearing element is pivotable between a first inactive position and a second active position, the shearing element shearing the fasteners during the second active position.

In another aspect a surgical stapling device comprises an end effector having first and second jaws pivotally coupled to one another and configured to engage tissue therebetween, a plurality of plastically deformable staples frangibly formed on a carrier and disposed within the first jaw, wherein the staples are configured to be rotatably deployed into tissue engaged between the jaws, a wedge configured to slidably advance through the first jaw to rotatably drive the staples into tissue, and a shearing element configured to shear the staples from the carrier after the staples are rotatably deployed into the tissue by the wedge. In one aspect the shearing element is positioned proximal of the wedge. In another aspect the wedge includes a plurality of upright flanges configured to rotatably drive the staples into tissue, and the shearing element includes a plurality of upright flanges configured to shear the staples from the carrier. The wedge can include a knife for cutting tissue engaged between the first and second jaws, and the shearing element can be positioned proximal of the knife.

In one aspect the shearing element is configured to shear the staples from the carrier during proximal movement of the shearing element through the first jaw. In another aspect the shearing element is pivotable between a first inactive position and a second active position, the shearing element shearing the staples during the second active position.

BRIEF DESCRIPTION OF THE DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Figure 1:
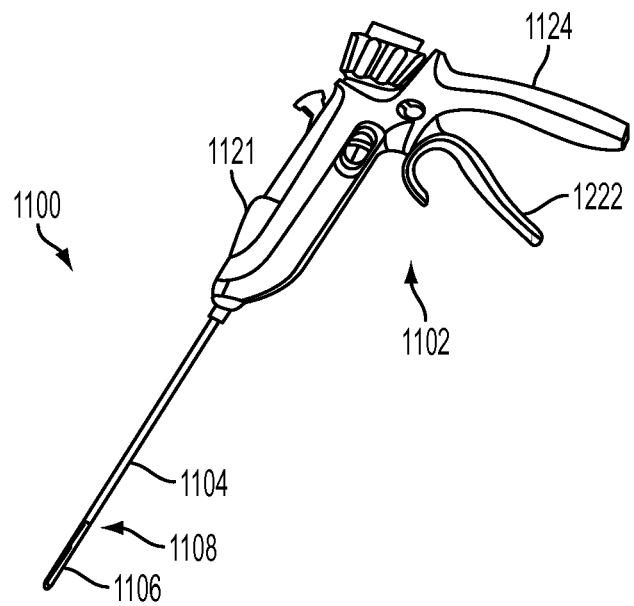
FIG. 1 is a perspective view of one embodiment of a surgical device configured to apply fasteners to tissue and including an end effector, the end effector being in a closed position.

FIG. 1 illustrates one embodiment of a surgical device 1100 that can be configured to apply staples to tissue. The device 1100 in this illustrated embodiment includes a linear stapler configured to apply linear rows of staples. Other embodiments of surgical devices that can be configured to apply staples to tissue are described in U.S. Pat. No. 5,465,895 entitled "Surgical Stapler Instrument" filed Feb. 3, 1994, U.S. Pat. No. 7,000,818 entitled "Surgical Stapling Instrument Having Separate Distinct Closing And Firing Systems" filed May 20, 2003, U.S. Pat. No. 7,669,746 entitled "Staple Cartridges For Forming Staples Having Differing Formed Staple Heights" filed on Aug. 31, 2005, and U.S. Pat. Pub. No. 2014/0175146 entitled "Microcutter Stapling Apparatus Clamp And Deploy Mechanisms Systems And Methods" filed Dec. 19, 2013, which are hereby incorporated by reference in their entireties.

Figure 2:
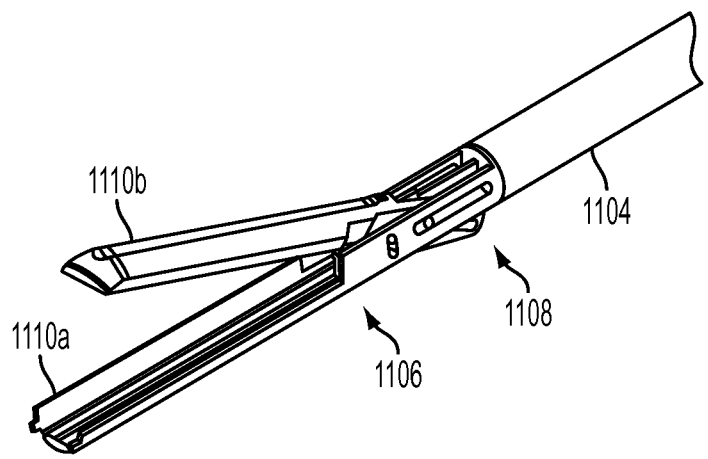
FIG. 2 is a perspective view of the end effector of FIG. 1 in an open position.
Figure 3:
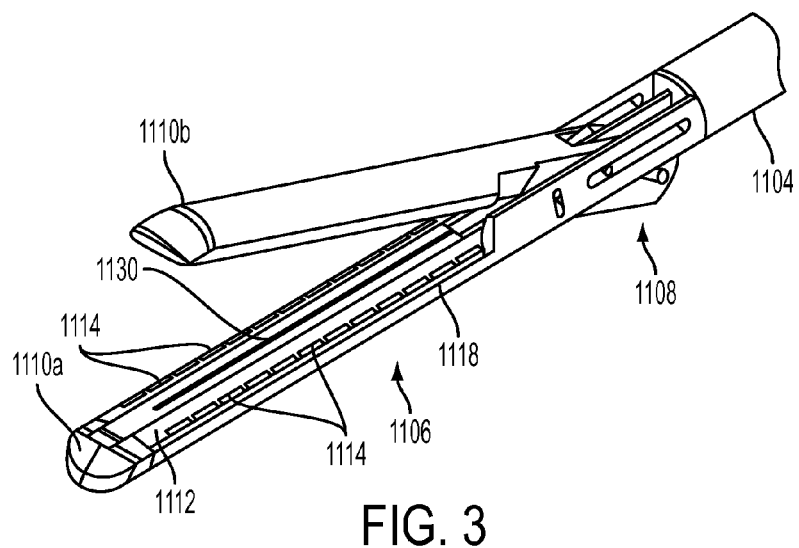
FIG. 3 is a perspective view of the end effector of FIG. 2 with one embodiment of a cartridge removably coupled thereto.

Referring again to FIG. 1, the device 1100 can include a proximal handle portion 1102 having an elongate shaft 1104 extending distally therefrom. As also shown in FIG. 2 and FIG. 3, the shaft 1104 can have an end effector 1106 coupled to a distal end thereof. The end effector 1106 can be coupled to the shaft 1104 at a pivot joint 1108. A proximal end of the end effector 1106 can be pivotally coupled to the joint 1108 at a distal end of the shaft 1104. The end effector 1106 in this illustrated embodiment includes a tissue grasper having a pair of opposed first and second jaws 1110a, 1110b configured to move between open and closed positions. The first jaw is also referred to herein as a "bottom jaw" and a "cartridge jaw," and the second jaw is also referred to herein as an "upper jaw" and an "anvil." As discussed further below, the handle portion 1102 can be configured to be manipulated to effect the opening and closing of the opposed jaws 1110a, 1110b, e.g., movement of one or both the jaws 1110a, 1110b about the pivot joint 1108, and the handle portion 1102 can be configured to be manipulated to effect the firing of staples (not shown) from a one of the jaws 1110a, 1110b, e.g., a bottom or cartridge one of the jaws 1110a. The staple firing can be independent of the opening and closing of the jaws 1110a, 1110b.

The handle portion 1102 can have a variety of sizes, shapes, and configurations. The handle portion 1102 can include a main housing 1121, which can house a variety of elements therein and can have some elements accessible outside thereof, such as a movable trigger 1122 and a stationary handle 1124. The movable trigger 1122 can be configured to be manually manipulated to move the movable trigger 1122 relative to the stationary handle 1124 so as to, e.g., effect closing of the jaws 1110a, 1110b.

The shaft 1104 can have a variety of sizes, shapes, and configurations. In an exemplary embodiment, the shaft 1104 can be rigid, e.g., made from a generally non-bendable material such as a metal (e.g., stainless steel, titanium, etc.) or a hard polymer. In other embodiments, the shaft 1104 can be configured to bend, such as being made from a generally flexible material, by including one or more articulation regions, etc. The shaft 1104 can have any longitudinal length, although in an exemplary embodiment it can be long enough to allow the handle portion 1102 to be manipulated outside a patient's body while the shaft 1104 extends through an opening in the body with the end effector 1106 disposed within a body cavity. In this way, the end effector 1106 can be easily manipulated when the device 1100 is in use during a surgical procedure. The shaft 1104 can have any diameter. For example, the shaft's diameter can be less than or equal to about 10 mm, e.g., less than or equal to about 7 mm, less than or equal to about 5 mm, etc., which can allow for insertion of the shaft 1104 through an minimally invasive access device, e.g., a trocar, a cannula, a multiport access device, etc., such as during a laparoscopic surgical procedure. The end effector 1106 coupled to the shaft's distal end can have a diameter equal to or less than the shaft's diameter, at least when the jaws 1110a, 1110b are in the closed position, which can facilitate insertion of the device's distal portion into a patient's body.

The end effector 1106 can have a variety of sizes, shapes, and configurations. In an exemplary embodiment, the end effector 1106 can be rigid. As shown in FIG. 2 and FIG. 3, the end effector 1106 including the first and second jaws 1110a, 1110b can be disposed at a distal end of the surgical device 1100. As in this illustrated embodiment, when the jaws 1110a, 1110b move between the open and closed positions, the second jaw 1110b can be configured to remain stationary relative to the shaft 1104, and the first jaw 1110a can be configured to move relative to the shaft 1104 and the second jaw 1110b by pivoting at the pivot joint 1108.

Figure 4:
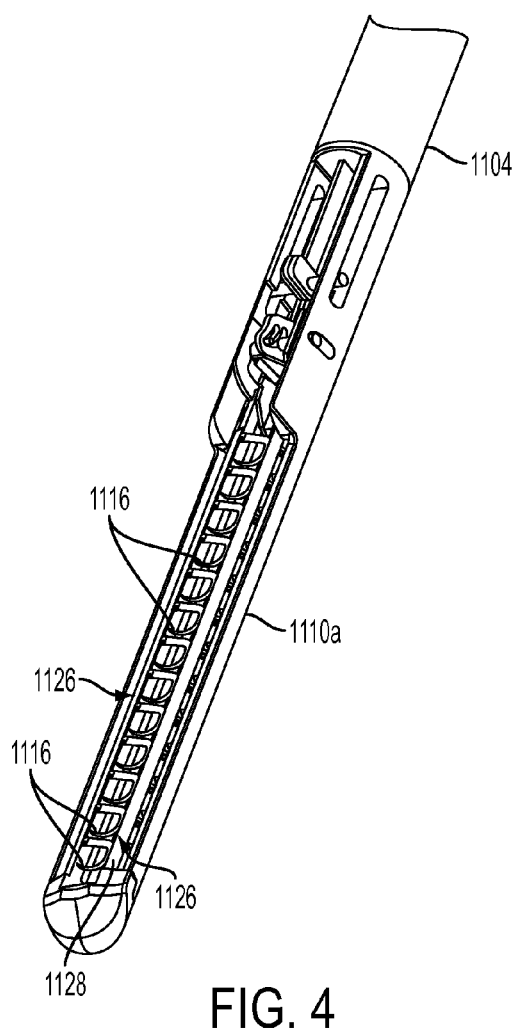
FIG. 4 is a perspective, partially cross-sectional view of the end effector and the cartridge of FIG. 3.

The end effector 1106 can be configured to releasably and replaceably seat a cartridge 1112 therein, as shown in FIG. 3 and FIG. 4. In this way, when the staples have been fired from the cartridge 1112, the cartridge 1112 can be removed from the second jaw 1110b and, optionally, replaced with another cartridge having another plurality of staples disposed therein. FIG. 2 shows the end effector 1106 without the cartridge 1112 seated therein. The end effector 1106 can be configured to receive the cartridge 1112 in the first jaw 1110a thereof, e.g., in a channel formed in the first jaw 1110a. The first jaw 1110a can be configured to seat cartridges of different sizes, thereby facilitating versatility of the device 1100.

Figure 5:
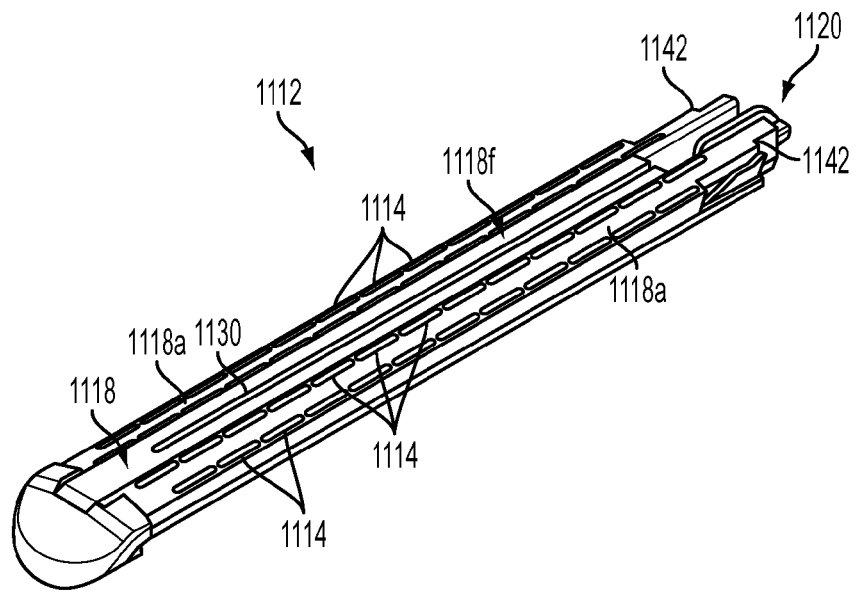
FIG. 5 is a perspective view of the cartridge of FIG. 3.
Figure 6:
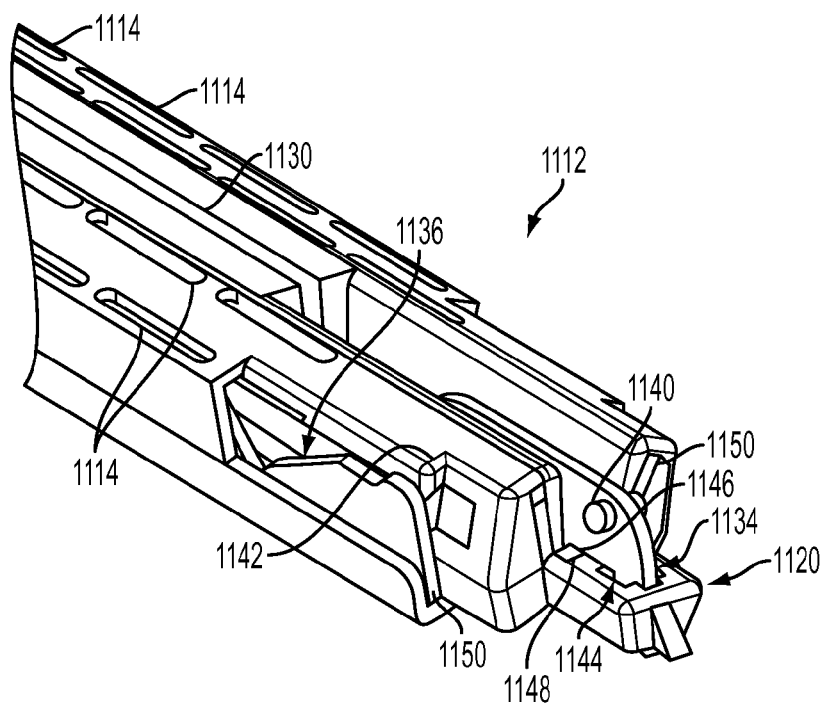
FIG. 6 is another perspective view of the cartridge of FIG. 3.
Figure 7:
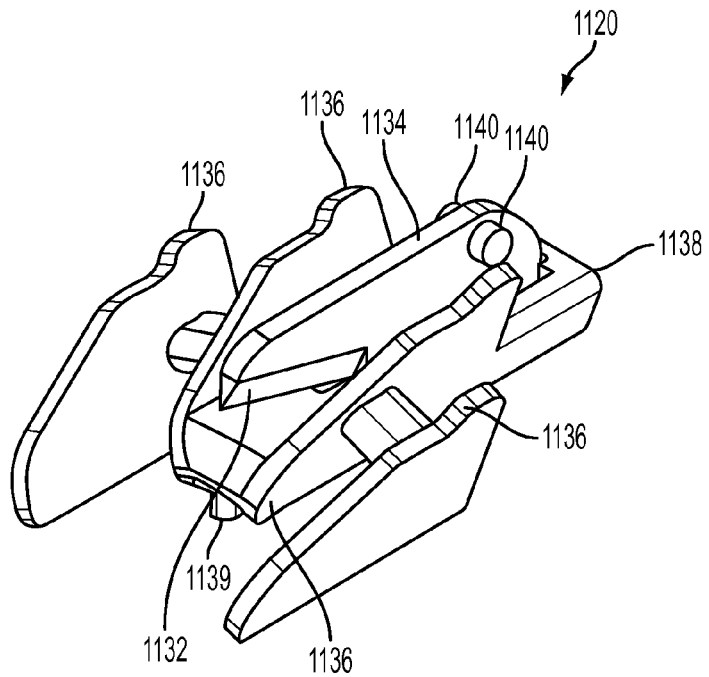
FIG. 7 is a perspective view of a sled of the cartridge of FIG. 3, the sled including a cutting element, and the cutting element being in a first position.
Figure 8:
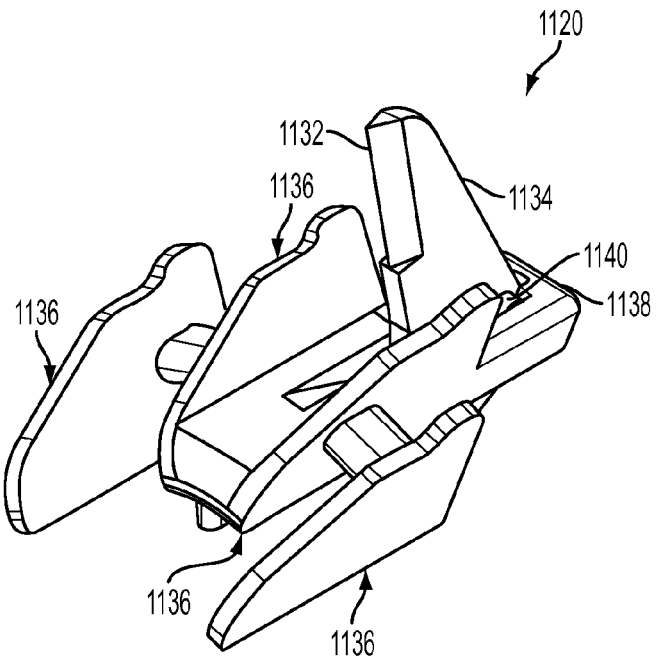
FIG. 8 is a perspective view of the sled of FIG. 7 with the cutting element in a second position that is different from the first position.

The cartridge 1112 can have a variety of sizes, shapes, and configurations, as will be appreciated by a person skilled in the art. As shown in FIG. 4, FIG. 5, and FIG. 6, the cartridge 1112 can include a sled 1120 and can have a plurality of staples 1116 disposed therein. The sled 1120 is also illustrated in FIG. 7 and FIG. 8. The cartridge 1112 can include a plurality openings 1114 formed in a tissue engaging surface 1118 thereof, as shown in FIG. 3, FIG. 5, and FIG. 6. The staples 1116 disposed in the cartridge 1112 can be configured to be ejected from the cartridge 1112 through the openings 1114, e.g., one staple 1116 out of each opening 1114 (as in this illustrated embodiment), two staples out of each opening 1114, etc. The openings 1114 can define staple-receiving recesses of the cartridge 1112 in which the staples 1116 are seated prior to being ejected from the cartridge 1112.

The staples 1116 can have a variety of sizes, shapes, and configurations. In this illustrated embodiment, the staples 1116 each have a D-shape and include a first leg that is substantially straight and a second leg that is curved. A person skilled in the art will appreciate that the first leg may not be precisely straight, e.g., due to manufacturing tolerances, but nevertheless be considered to be substantially straight. Each of the staples 1116 can be configured to be plastically deformable such that the staples 1116 can each be configured to change shape, such as when the staple 1116 is pressed against a tissue engaging surface (not shown) of the first jaw 1110a that faces the tissue engaging surface 1118 of the second jaw 1110b, while remaining a single unit, e.g., without either of the first and second legs breaking. A gap of space can exist between a terminal end of the first leg and a terminal end of the second leg. In other words, the "D" shape can have a gap therein. The gap of space can facilitate plastic deformation of the staple 1116.

The staples 1116 can each be frangibly attached to a carrier 1126, also referred to herein as a "carrier strip," disposed within the cartridge 1112. The staples 1116 can be frangibly attached to the carrier 1126 by, e.g., being stamped together with the carrier 1126 such that the staples 1116 and the carrier 1126 forms a single piece. The staples 1116 can each be configured to detach from the carrier 1126 when fired from the cartridge 1112. In some embodiments, some or all of the staples 1116 can be frangibly attached to another element, such as another element disposed within the cartridge 1112, an inner surface of the cartridge 1112, the tissue-engaging surface 1118 of the cartridge 1112, etc. The carrier 1126 can be fixedly attached to an upper surface of one or more rails 1128 defined by the cartridge 1112. The carrier 1126 can be configured to remain stationary relative to the cartridge 1112.

As shown in FIG. 3, FIG. 5, and FIG. 6, the cartridge 1112 can have a longitudinal slot 1130 formed therein. The longitudinal slot 1130 can extend along a substantially flat central portion 1118f of the tissue-engaging surface 1118. The slot 1130 can be configured to have a cutting element such as a knife (not shown) extend therethrough so as to be configured to cut tissue engaged by the tissue-engaging surface 1118, as discussed further below. The openings 1114 can be formed in angled portions 1118a of the tissue-engaging surface 1118 on both sides of the slot 1130, as shown in FIG. 3, FIG. 5, and FIG. 6. In some embodiments, the tissue-engaging surface 1118 can be substantially flat, e.g., not have angled portions, while in other embodiments, the tissue-engaging surface 1118 can be angled, e.g., not have any substantially flat portions.

As shown in FIG. 5 and FIG. 6, the cartridge 1112 can include a gap-setting feature 1142 configured to set of gap of space between the first and second jaws 1110a, 1110b when the jaws 1110a, 1110b are closed and the cartridge 1112 is seated in the second jaw 1110b. In this way, the gap-setting feature 1142 can be configured to define a minimum distance between the facing tissue-engaging surfaces of the first and second jaws 1110a, 1110b. The gap-setting feature 1142 can have a variety of sizes, shapes, and configurations. As in this illustrated embodiment, the gap-setting feature 1142 can include an indentation inward toward a lateral center of the cartridge 1112, where a portion of a lateral edge of the cartridge 1112 immediately proximal to the gap-setting feature 1142 is located laterally inward relative to a portion of a lateral edge of the cartridge 1112 located immediately distal to the gap-setting feature 1142.

The sled 1120 of the cartridge 1112 can have a variety of sizes, shapes, and configurations. The sled 1120 can be configured to translate longitudinally along the cartridge 1112 to cause deployment of the staples 1116 therefrom and to cause tissue engaged by the end effector 1106 to be cut with the cutting element extending through the slot 1130. The staples 1116 can be arranged longitudinally in the cartridge 1112, as shown in FIG. 4, and the sled 1120 can be configured to sequentially engage the longitudinally arranged staples 1116 as the sled 1120 translates longitudinally. As illustrated in FIG. 7 and FIG. 8, the sled 1120 can include a plurality of wedges 1136 and can include a cutting element 1134, which in this illustrated embodiment includes a knife with a blade 1132. The sled 1120 in this illustrated embodiment includes four wedges 1136 but the sled 1120 can include another number of wedges 1136 as appropriate for the arrangement of the staples 1116 in the cartridge 1112. Each of the wedges 1136 can have a shape configured to cause the staples 1116 contacted by that wedge 1136 to move upward toward the second jaw 1110b through the openings 1114 and deform against the second jaw 1110b. As shown in FIG. 6, the cartridge 1112 can include a plurality of longitudinal slots 1150 formed therein, each of the slots 1150 being configured to slidably receive one of the wedges 1136 therein. The slots 1150 can facilitate consistent, straight movement of the wedges 1136 through the cartridge 1112 to help ensure proper engagement of the wedges 1136 with the staples 1116.

Each of the wedges 1136 can be attached to a base 1138 of the sled 1120 and can be in a fixed position relative thereto. The base 1138 can have a guide element 1139 extending generally downward therefrom. The guide element 1139 can be configured to slide within a channel formed in the cartridge 1112 that includes the sled 1120. The cutting element 1134 can also be attached to the base 1138, but the cutting element 1134 can be configured to move relative to the base 1138. The cutting element 1134 can be substantially laterally centered in the base 1138, which can facilitate substantially central positioning of the cutting element 1134 relative to tissue engaged by the end effector 1106.

The cutting element 1134 can be configured to be movable relative to a remainder of the sled 1120 between a first position, shown in FIG. 7, and a second position, shown in FIG. 6 and FIG. 8. The first position can be an initial position of the cutting element 1134. In the first position, also referred to herein as a "stowed position," the blade 1132 can be generally obscured, e.g., oriented generally downward as shown in the embodiment of FIG. 4, FIG. 5, FIG. 6, and FIG. 7, which can help prevent the blade 1132 from inadvertent cutting, such as accidentally cutting a user of the device 1100 during seating of the cartridge 1120 within the end effector 1104 and/or premature cutting of tissue engaged by the end effector 1104. The base 1138 can have a cavity 1144 formed therein, as shown in FIG. 6, which can be configured to seat the cutting element 1134 at least partially therein when the cutting element 1134 is in the first position. In the second position, also referred to herein as an "upright position," the blade 1132 can be generally unobscured and facing a distal direction as shown in the embodiment of FIG. 6 and FIG. 8, which can allow the blade 1132 to extend through the slot 1130 and cut tissue engaged by the end effector 1106.

The sled 1120 can include a pivot member 1140 configured to facilitate movement of the cutting element 1134 relative to the remainder of the sled 1120. The pivot member 1140 can have a variety of sizes, shapes, and configurations. The pivot member 1140 can be attached to the cutting element 1134 such that engagement of the pivot member 1140 can cause the cutting element 1134 to pivot about a pivot point so as to move relative to the remainder of the sled. As in this illustrated embodiment the pivot member 1140 can include two separate pins extending laterally from opposite sides of the cutting element 1134. In other embodiments, the pivot member 1140 can include a single pin extending through the cutting element 1134 to extend laterally from opposite sides therefrom, a single pin extending laterally from one side of the cutting element 1134, etc. At the pivot point, the sled 1120 can include a pivot axle 1146 extending laterally from the cutting element 1134, and can include an axle cavity 1148 formed in the base 1138 and configured to receive the pivot axle 1146 therein.

The surgical devices described herein can be used in a variety of surgical procedures. In an exemplary embodiment, the procedure can be a minimally invasive procedure in which the surgical device can be advanced into a body of a patient through a relatively small opening in the patient. In a minimally invasive surgical procedure, one or more introducer devices (not shown), e.g., a cannula, a trocar, etc., can be advanced through an opening in the patient to provide access to a surgical site. A person skilled in the art will appreciate that one or more viewing devices, e.g., a scoping device such as an endoscope, can be advanced into the body through the incision or through another opening, e.g., another incision or a natural orifice, to provide visualization of the surgical site from outside the body. As will be appreciated by a person skilled in the art, the surgical device can be advanced into the patient's body in a variety of ways, such as by being inserted transorally therein, inserted through an introducer device, inserted through a scoping device, inserted directly through an incision, etc. Although the following embodiment of use of a surgical device in a surgical procedure is described with respect to the device 1100 of FIG. 1, any of the surgical devices described herein can be similarly used.

The surgical devices described herein can have any one or more variations to facilitate effective use of the device. Examples of such variations are described further below.

In some embodiments, a surgical device such as the above-mentioned surgical device 1100 can be configured to facilitate ejection of fasteners from a cartridge that has the fasteners disposed therein. In general, the device can include at least one separation feature configured to facilitate complete removal of one or more fasteners from within the cartridge. The fasteners can thus each be more likely to be deployed into and remain within the tissue after a firing operation ejecting the fasteners into the tissue, thereby facilitating complete sealing of the tissue with the fasteners and/or facilitating healing of the tissue. The at least one separation feature can be configured to facilitate complete ejection of the one or more fasteners after the one or more fasteners have been deformed by an anvil, which can significantly reduce a force required to fire the one or more fasteners from the cartridge. In other words, a force to fire can be reduced as fastener forming and fastener disconnection can be timed separately with the fastener being deformed prior to the fastener being fully disconnected from the cartridge. In an exemplary embodiment, the device can be configured to facilitate disconnection of fasteners from a carrier to which the fasteners are frangibly attached. In general, the device can include a separation feature in the form of a shearing element configured to facilitate separation of the fasteners from the carrier when the fasteners are deployed from a cartridge that has the fasteners and the carrier disposed therein. The shearing element can be disposed between a sled of the device and a drive beam of the device, which can facilitate complete ejection of the one or more fasteners after the one or more fasteners have been urged toward the anvil by the sled.

The surgical device can be configured to facilitate ejection of fasteners from a cartridge in a variety of ways. In the embodiments described below, staples are used as examples of fasteners, but as will be appreciated by a person skilled in the art, other types of fasteners can be similarly configured and used. In exemplary embodiments, the fasteners can be D-shaped fasteners such as the above-mentioned staples 1116.

Figure 9:
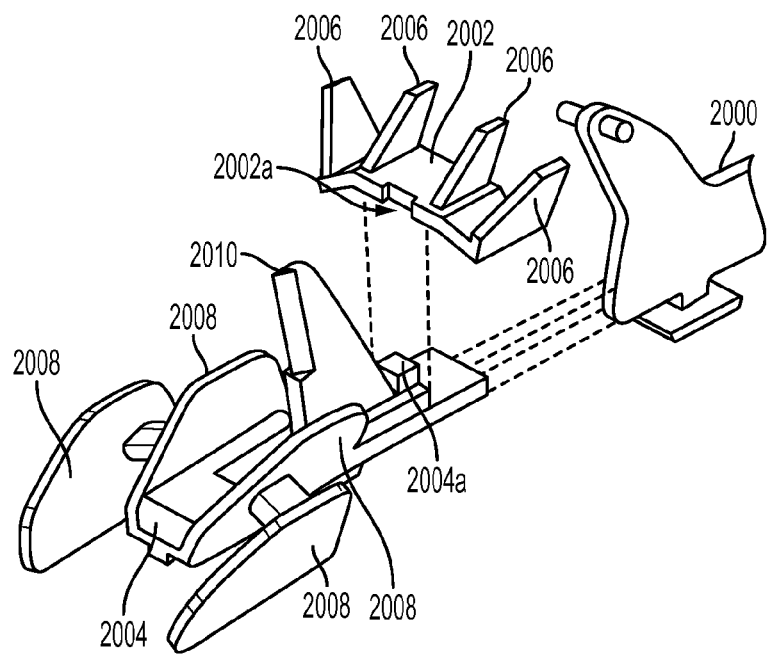
FIG. 9 is a perspective view of one embodiment of a shearing element configured to couple to a sled and an I-beam and be positioned therebetween.
Figure 10:
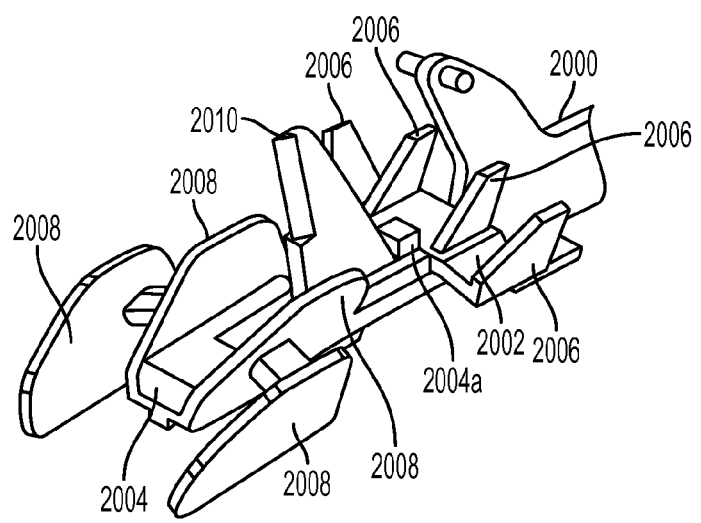
FIG. 10 is a perspective view of the shearing element of FIG. 9 positioned between and coupled to the sled and the I-beam.

FIG. 9 and FIG. 10 illustrate one embodiment of a separation feature 2002 configured to facilitate ejection of fasteners (not shown) from a cartridge (not shown) that has the fasteners disposed therein and connected to a carrier (not shown). As in this illustrated embodiment, the separation feature 2002 can include a shearing element configured to shear one or more of the fasteners from a carrier (not shown) to which the one or more fasteners are frangibly attached. The shearing element 2002 can be coupled to a sled 2004 configured to urge the fasteners out of the cartridge, as discussed herein. The shearing element 2002 can be a discrete element from the sled 2004, as shown in FIG. 9, or the shearing element and the sled can be integrally formed. When the shearing element 2002 is independent from the sled 2004 as in this illustrated embodiment, the sled 2004 and the shearing element 2002 can include corresponding mating features 2002a, 2004a configured to securely couple the sled 2004 and the shearing element 2002 together.

The shearing element 2002 can have a variety of sizes, shapes, and configurations. As in this illustrated embodiment, the shearing element 2002 can include a plurality of shearing wedges 2006 each configured to shear at least one fastener from the carrier. In an exemplary embodiment, a number of the shearing wedges 2006 can equal a number of the sled's wedges 2008 such that each of the fasteners deployed by a one of the wedges 2008 can be sheared by an associated one of the shearing wedges 2006. The shearing wedges 2006 can generally extend upright and be oriented at angles corresponding to the sled's wedges 2006. In an exemplary embodiment, the shearing wedges 2006 can be taller than the sled's wedges 2008, e.g., extend thereabove when the shearing element 2002 and the sled 2004 are coupled together as shown in FIG. 10. This greater upward reach of the shearing wedges 2006 can help ensure that the shearing wedges 2006 contact the fasteners so as to shear the fasteners. The shearing wedges 2006 may in some embodiments have enough upward reach that they can slide against and/or otherwise contact the cartridge when translating therethrough, which may damage the cartridge. However, releasable and replaceable cartridges are typically used only once, e.g., to once eject fasteners disposed therein, such that damaging the cartridge does not affect effective use of the cartridge.

The shearing wedges 2006 can be sharp, e.g., have sharpened edges, which can help break deployed fasteners off the carrier. The shearing wedges 2006 can be sharp and/or can extend upward of the sled's wedges 2008.

As shown in FIG. 9 and FIG. 10, the shearing element 2002 can be positioned on a proximal side of the sled 2004. The shearing element 2002 can thus be positioned proximal to the wedges 2008 of the sled 2004. The sled 2004 includes four wedges 2008 in this illustrated embodiment, but as mentioned above, a sled can include any number of wedges. In an exemplary embodiment, at least the wedges 2006 of the shearing element 2002 can be positioned entirely proximal to the wedges 2008 of the sled 2004, as in this illustrated embodiment, which can help ensure that the fasteners have been pushed upward as fully as possible by the wedges 2008 prior to the shearing element 2002 shearing the fasteners from the carrier. The shearing element 2002 can be positioned proximal to a cutting element 2010 of the sled 2004, which in this illustrated embodiment includes a knife similar to the above-mentioned cutting element 1134. In an exemplary embodiment, at least the wedges 2006 of the shearing element 2002 can be positioned entirely proximal to the cutting element 2010, as in this illustrated embodiment, which can allow tissue to be cut and fasteners to be deployed into the tissue before the shearing element 2003 facilitates complete detachment of the fasteners from the carrier.

The shearing element 2002 can be disposed within a cartridge. In this way, when the cartridge is configured to be releasably and replaceably coupled to an end effector, the shearing element 2002 can also be so coupled.

A drive beam 2000 can be configured to advance the sled 2004 distally through the cartridge, as discussed herein. Thus, the drive beam 2000 can also be configured to advance the shearing element 2002 distally through the cartridge when the drive beam 2000 advances the sled 2004 therethrough.

Figure 11:
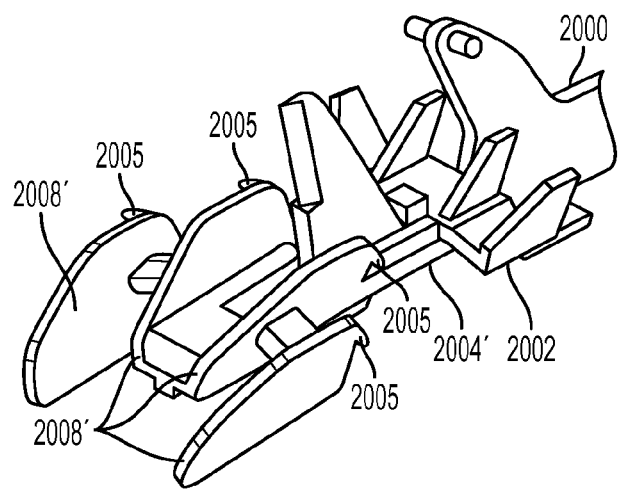
FIG. 11 is a perspective view of the shearing element of FIG. 9 coupled to another embodiment of a sled and to the I-beam of FIG. 9.

FIG. 11 illustrates an alternate embodiment of a sled 2004' that can be configured and used similar to the sled 2004 of FIG. 9 and FIG. 10. Each wedge 2008' of the sled 2004' of FIG. 3 includes a protrusion 2005 extending laterally therefrom. A wedge's protrusion 2005 can be configured to crimp a fastener (not shown) pushed by that wedge 2008', which can help ensure that the fastener is fully crimped, e.g., fully closed, before the shearing element 2002 shears the fastener from the carrier.

As in the embodiments of FIG. 9, FIG. 10, and FIG. 11, the sled 2004 and the shearing element 2002 can be configured to remain in a distal portion of the cartridge after the I-beam 2000 has advanced the sled 2004 and the shearing element 2002 distally through the cartridge. In other words, proximal retraction of the I-beam 2000 through the cartridge after firing of the fasteners does not proximally retract the sled 2004 or the shearing element 2002. The shearing element 2002 thus performs all shearing during distal movement of the shearing element 2002 through the cartridge. In some other embodiments, a sled and a shearing element can be configured to be proximally retracted after an I-beam has advanced the sled and the shearing element distally through a cartridge. The shearing elements in these embodiments can perform all shearing during proximal movement of the shearing element through the cartridge. The fasteners can all be ejected from the cartridge during the distal movement of the sled and the cartridge such that all shearing by the shearing element can be performed after all of the fasteners have been deployed from the cartridge.

Figure 12:
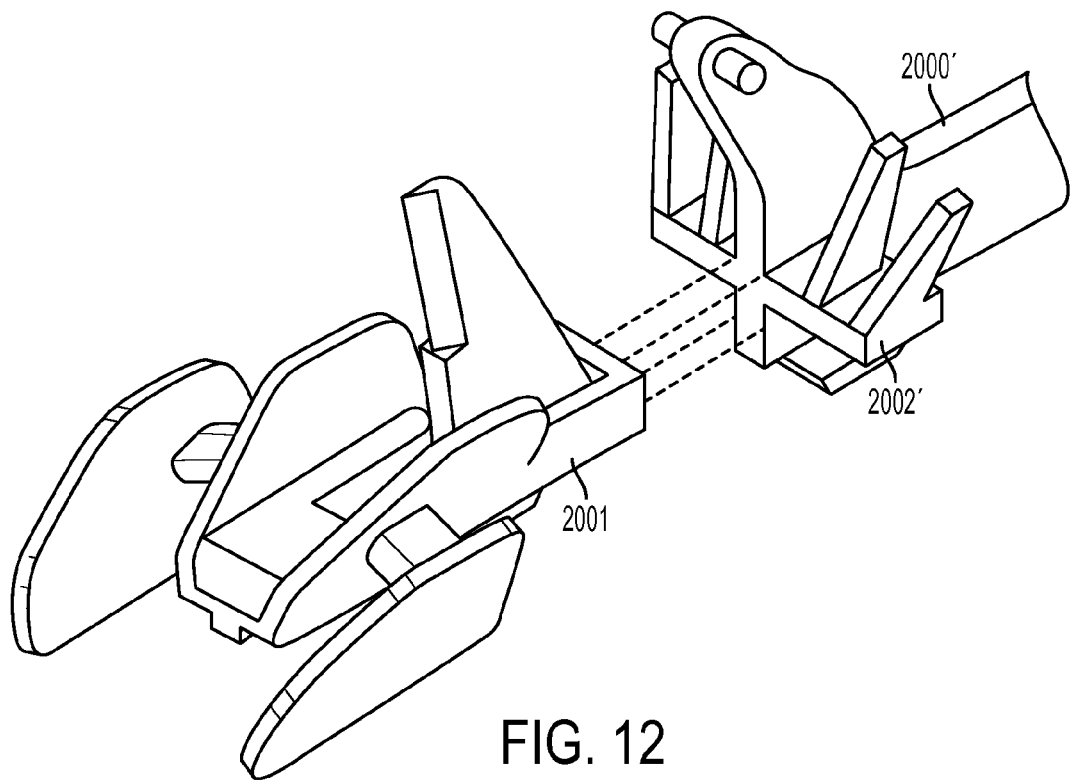
FIG. 12 is a perspective view of another embodiment of a shearing element configured to couple to a sled and an I-beam and be positioned therebetween.
Figure 13:
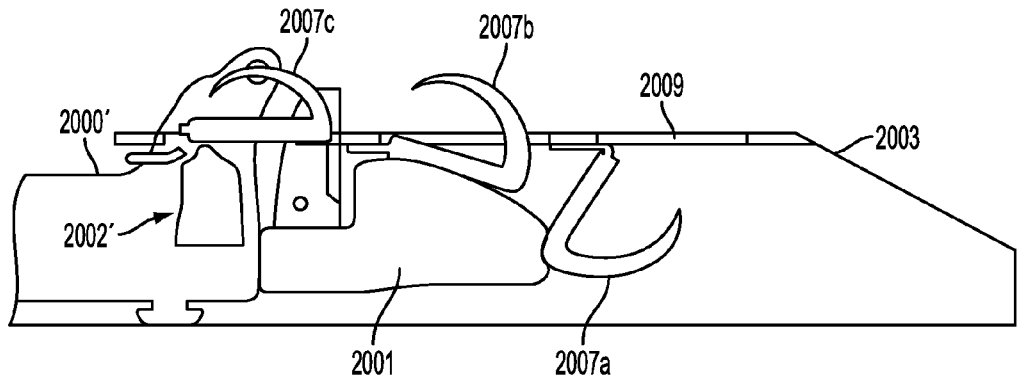
FIG. 13 is a side cross-sectional view of the shearing element, sled, and I-beam of FIG. 12 firing fasteners from a bottom jaw of an end effector.

FIG. 12 illustrates an alternate embodiment of a shearing element 2002' that can be configured and used similar to the shearing element 2002 of FIG. 9 and FIG. 10 except that in this illustrated embodiment, the shearing element 2002' is coupled to an I-beam 2000' instead of to a sled 2001. The shearing element 2002' can thus be included as an integral part of a surgical device, as opposed to being part of a cartridge removably and replaceably attachable to a surgical device. FIG. 13 illustrates the shearing element 2002' disposed within a cartridge (not shown) seated in a bottom jaw 2003 and including a plurality of fasteners 2007a, 2007b, 2007c frangibly attached to a carrier 2009. Two of the fasteners 2007a, 2007b are shown frangibly attached to the carrier 2009. A third one of the fasteners 2007c is shown detached from the carrier 2009, e.g., having been sheared thereof by the shearing element 2002'.

Figure 14:
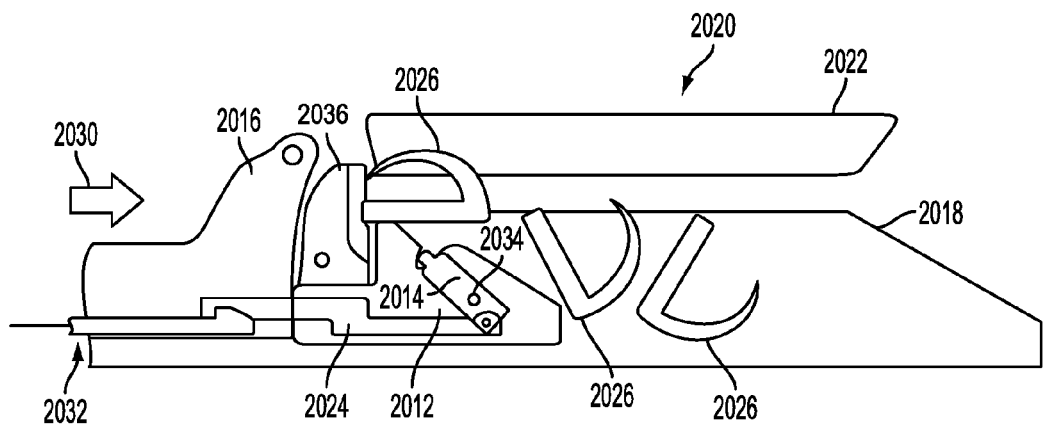
FIG. 14 is a side cross-sectional view of another embodiment of a shearing element, the shearing element being coupled to a sled and an I-beam translating distally through a bottom jaw of an end effector, the shearing element being in a first position.
Figure 15:
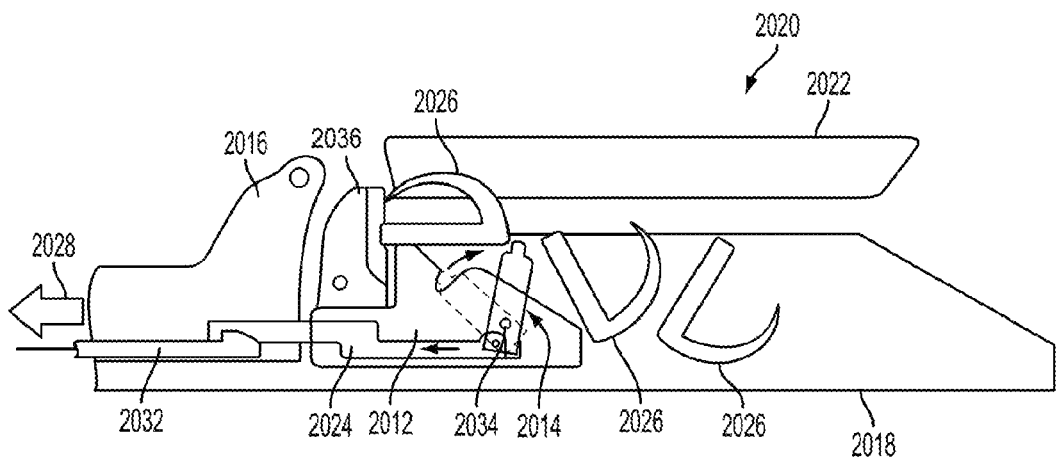
FIG. 15 is a side cross-sectional view of the shearing element, sled, and I-beam of FIG. 14 translating proximally through the bottom jaw, the shearing element being in a second position that is rotated from the first position.

FIG. 14 and FIG. 15 illustrate one embodiment of a sled 2012 and a shearing element 2014 coupled to the sled 2012 that are configured to be proximally retracted in a proximal direction 2028 after an I-beam 2016 has advanced the sled 2012 and the shearing element 2014 distally through a bottom jaw 2018 in a distal direction 2030. The jaw 2018 in this illustrated embodiment is part of an end effector 2020 that also includes an anvil 2022, and has a cartridge (not shown) releasably and replaceably seated in the bottom jaw 2018.

The shearing element 2014 can have a variety of sizes, shapes, and configurations. As in this illustrated embodiment, the shearing element 2014 can include a movable bar. The shearing element 2014 can be movable between a first position, shown in FIG. 14, in which the sled 2012 nests the shearing element 2014, and a second position, shown in FIG. 15, in which the shearing element 2014 extends upwardly above the sled 2012. The shearing element 2014 in the first position can be configured to not shear any fasteners 2026, and the shearing element 2014 in the second position can be configured to shear fasteners 2026. The shearing element 2014 can be configured to move from the first position to the second position, e.g., pivot about a pivot joint 2034, in response to a drive bar 2032 coupled to the drive beam 2016 being moved proximally so as to proximally retract the drive beam 2016. The shearing element 2014 can thus be configured to automatically move from the first position to the second position.

The cartridge can include an attachment bar 2024 configured to removably couple to the drive bar 2032. In response to the cartridge being seated in the bottom jaw 2018, the attachment bar 2024 can clip onto the drive bar 2032, e.g., by a protrusion at a proximal end of the attachment bar 2024 engaging a corresponding protrusion at a distal end of the drive bar 2032. Thus, when the drive bar 2032 moves distally or proximally, the attachment bar 2024 can also move distally or proximally. The attachment bar 2024 can be attached to the sled 2012 such that the movement of the attachment bar 2024 can also cause movement of the sled 2012 and the shearing element 2014 attached thereto. FIG. 14 shows the drive bar 2032 coupled to the attachment bar 2024 and advancing distally in the distal direction 2030 so as to advance the sled 2012 distally with a cutting element 2036 of the sled 2012 pivoted to an upright position and with the shearing element 2014 in the first position. FIG. 15 shows the drive bar 2032 coupled to the attachment bar 2024 and advancing proximally in the proximal direction 2028 so as to advance the sled 2012 proximally with a cutting element 2036 of the sled 2012 in the upright position and with the shearing element 2014 in the second position. Moving the drive bar 2032 proximally can cause the shearing element 2014 to pivot from the first position to the second position since the pivot joint 2034 about which the shearing element 2014 can be configured to pivot can be an attachment point between the shearing element 2014 and the attachment bar 2024.

Figure 16:
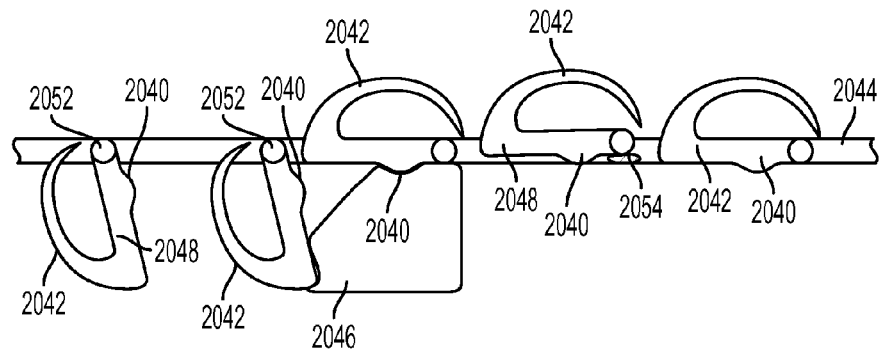
FIG. 16 is a side view of one embodiment of a plurality of fasteners each including a separation feature and each being frangibly attached to a carrier strip, a sled translating relative to the fasteners and the carrier and engaging one of the separation features.
Figure 17:
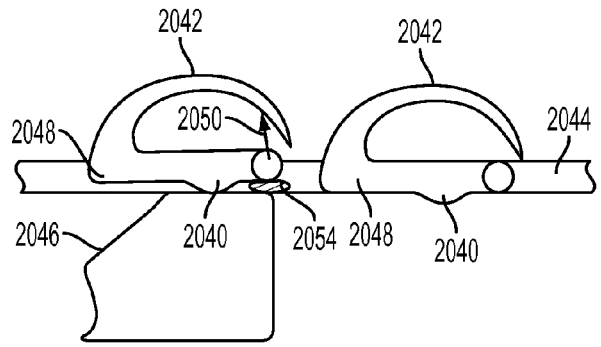
FIG. 17 is a side view of the sled and one of the fasteners of FIG. 16.

In some embodiments, a separation feature can be formed on a fastener. FIG. 16 and FIG. 17 illustrate another embodiment of a separation feature 2040 formed on a fastener 2042 and configured to facilitate ejection of the fastener 2042 from a cartridge (not shown) that has the fastener 2042 disposed therein and connected to a carrier strip 2044. As in this illustrated embodiment, the separation feature 2040 can include a bump formed on the fastener 2042 and configured to engage a sled 2046.

The bump 2040 can have a variety of sizes, shapes, and configurations. The bump 2040 can be formed on a substantially straight leg 2048 of the fastener 2042 and can be formed on an outward-facing surface thereof, thereby allowing the sled 2046 to engage the bump 2040 when contacting and deploying the fastener 2040. The bump 2040 can be configured to bias the fastener 2042 in an upward direction 2050, e.g., toward an anvil coupled to a jaw having the cartridge seated therein. This bias can increase stress on the fastener 2042 at a joint 2052 where the fastener 2042 is frangibly connected to the carrier 2044, thereby allowing the fastener 2042 to more reliably disconnect from the carrier strip 2044. A size of the bump 2040 can be tuned to the stress needed to disconnect the fastener 2042 from the carrier 2044. FIG. 16 and FIG. 17 show one of the fasteners 2042 disconnected from the carrier 2044 such that the joint where the fastener 2042 was frangibly connected to the carrier 2044 is now a broken joint 2054.

In some embodiments, a sled can include a separation feature in the form of a bump similar to the above-mentioned bump 2040. The sled can include the bump in alternative to or in addition to a fastener including a bump such as the above-mentioned bump 2040. The sled and the fastener each including a bump can exert more stress on a joint where the fastener frangibly connects to a carrier than when only one of the sled and the fastener includes a bump, which can allow the fastener to more reliably disconnect from the carrier.

Figure 18:
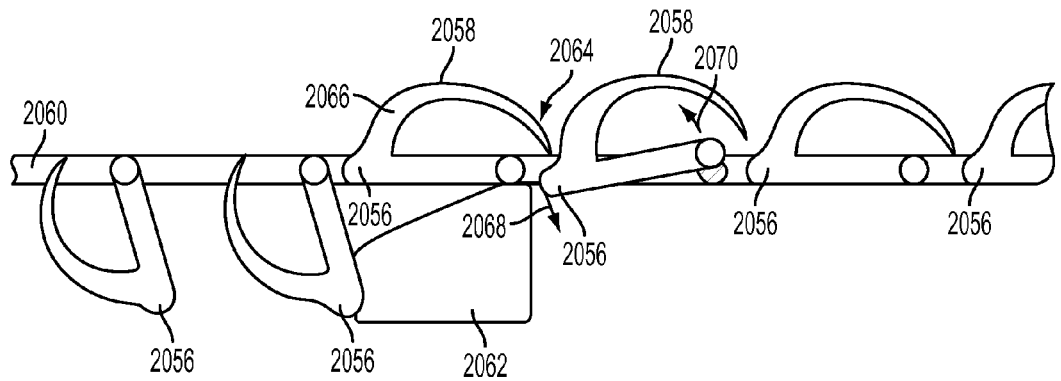
FIG. 18 is a side view of another embodiment of a plurality of fasteners each including a separation feature and each being frangibly attached to a carrier strip, a sled translating relative to the fasteners and the carrier.

FIG. 18 illustrates another embodiment of a separation feature 2056 formed on a fastener and configured to facilitate ejection of the fastener 2058 from a cartridge (not shown) that has the fastener 2058 disposed therein and connected to a carrier strip 2060. Similar to the above-mentioned separation feature 2040, the separation feature 2056 can include a bump formed on the fastener 2056. However, in this illustrated embodiment, the separation feature 2056 is formed at a distal end of the fastener 2058, with the fastener's distal end being with reference to the fastener's position as deployed from a sled 2062 translating distally through the cartridge. The bump 2056 being formed at the fastener's distal end can allow the bump 2056 to engage the fastener 2058 being deployed immediately after the fastener 2056 having its bump 2056 positioned distally with reference to the fastener's position as deployed from the sled 2062. More particularly, a pointed tip 2064 of the fastener's curved leg 2066 can be configured to push against the bump 2056 of the fastener 2056 longitudinally aligned therewith and deployed immediately prior to the fastener 2056 whose tip 2064 pushes the bump 2056, as shown by an arrow 2068. This force applied to the bump 2056 can facilitate detachment from the carrier 2060 of the fastener 2956 whose bump 2056 is being pushed, as shown by an arrow 2070.

In some embodiments, a separation feature can be formed on a cartridge, e.g., the above-mentioned cartridge 1112. In general, the separation feature being formed on the cartridge can be configured to provide counter resistance to a fastener, e.g., the above-mentioned fastener 1116, after the fastener has been pushed upward by a sled, e.g., the sled, and formed. The separation feature can thus help ensure that the fastener disconnects from a carrier to which the fastener is frangibly attached within the cartridge pre-deployment.

Figure 19:
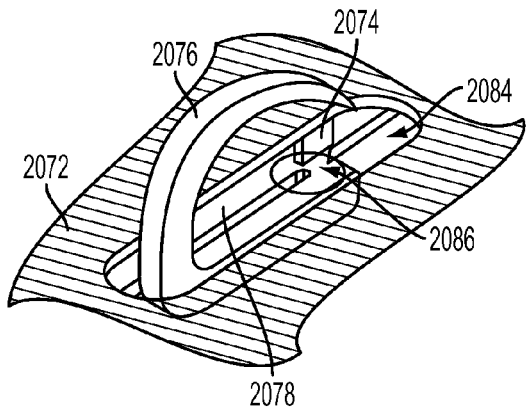
FIG. 19 is a perspective view of one embodiment of a cartridge including a separation feature formed thereon adjacent to a fastener ejectable from the cartridge and frangibly attached to a carrier.
Figure 20:
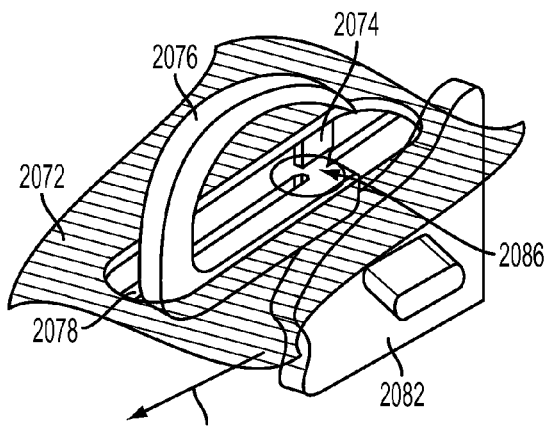
FIG. 20 is a perspective view of the fastener of FIG. 19 translating distally and engaging the fastener.
Figure 21:
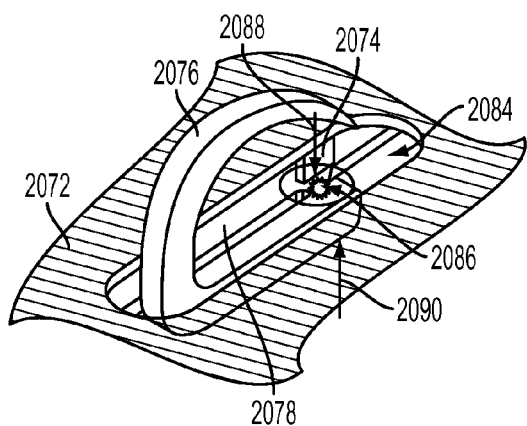
FIG. 21 is a perspective view of the separation feature of FIG. 19 facilitating separation of the fastener of FIG. 20 from the carrier.

FIG. 19, FIG. 20, and FIG. 21 illustrate an embodiment of a cartridge 2072 that includes a plurality of separation features 2074 that can each be configured to facilitate separation of one of a plurality of fasteners 2076 disposed within the cartridge 2072 and frangibly attached to a carrier 2078 disposed within the cartridge 2072. The separation feature 2074 can have a variety of sizes, shapes, and configurations. As in this illustrated embodiment, the separation feature 2074 can include a wall extending upward-downward, e.g., in a direction substantially perpendicular to a direction 2080 in which a sled 2082 can be configured to translate to eject the fasteners 2074 from the cartridge 2072 through openings 2084 formed in the cartridge 2072. For ease of illustration, the sled 2082 is only partially shown in FIG. 20. The wall is rectangular shaped in this illustrated embodiment, but the wall can have other shapes, e.g., square, semi-circular, triangular, etc. In other embodiments, instead of a wall, the separation feature 2074 can include a protrusion, such as a bump, extending from a surface of the cartridge 2072.

Each of the separation features 2074 can be positioned adjacent to a connection point 2086 where its associated fastener 2076 is frangibly attached to the carrier 2078. As in this illustrated embodiment, the separation feature 2074 can be adjacent to and positioned above the connection point 2086. When the sled 2082 translates in the direction 2080, e.g., distally, as shown in FIG. 20, the sled 2082 can cause the fastener 2076 to rotate out of the opening 2084 to be deployed, as discussed herein. As shown in FIG. 21, the separation feature 2074 can be configured to exert a force 2088, e.g., a downward directed force, that opposes a force 2090, e.g., an upward directed force, exerted by the sled 2082. The separation feature's force 2088 can resist the sled's force 2090, thereby facilitating breakage of the fastener 2074 from the carrier 2078 at the connection point 2086.

FIG. 22, FIG. 23, FIG. 24, FIG. 25, and FIG. 26 illustrate another embodiment of a cartridge 2092 that includes a separation feature 2094 that can be configured to facilitate separation of one of a plurality of fasteners 2096 disposed within the cartridge 2092. In this illustrated embodiment, the fasteners 2096 can be disposed within the cartridge 2092 as discrete elements not attached to a carrier, e.g., each of the fasteners 2096 can be disposed in its own pocket formed in the cartridge 2092 below a tissue-engaging surface 2100 of the cartridge 2092. Fasteners being discrete element unattached to a carrier can better guide fasteners during fastener forming and/or can help prevent the fastener from having any jagged edges where the fastener detaches from a carrier. Such jagged edges can be sharp and/or otherwise irritating to tissue in which the fastener is secured. The pocket can have a shape corresponding to a shape of the fastener, which can facilitate rotational forming of the fastener and/or facilitate easy separation of the fastener from the cartridge.

The separation feature 2094 in this illustrated embodiment includes a retainer plate. The retainer plate 2094 can have a variety of sizes, shapes, and configurations. The retainer plate 2098 can define the tissue-engaging surface 2100 and can have a plurality of openings 2102 formed therein through which the fasteners 2096 can be ejected from the cartridge 2092. Each of the openings 2102 can include a first slot extending in a proximal-distal direction and a second slot extending laterally and substantially perpendicular to the first slot such that the opening 2102 can have a "T" shape or a cross shape. The openings 2102 each have a cross shape in this illustrated embodiment. The fasteners 2096 can each include a retention pin 2104 configured to move through the opening 2102, e.g., the second slot thereof, when aligned therewith. The retention pin 2104 can be formed adjacent a proximal end of the fastener 2096, as in this illustrated embodiment, with the fastener's proximal end being with reference to the fastener's position as deployed from a sled 2106 translating in a distal direction 2110 through a bottom jaw 2108 having the cartridge 2092 seated therein. The openings 2102 can thus be configured as key holes through which the fasteners 2096 can be configured to pass so as to be fired out of the cartridge 2092.

Figure 22:
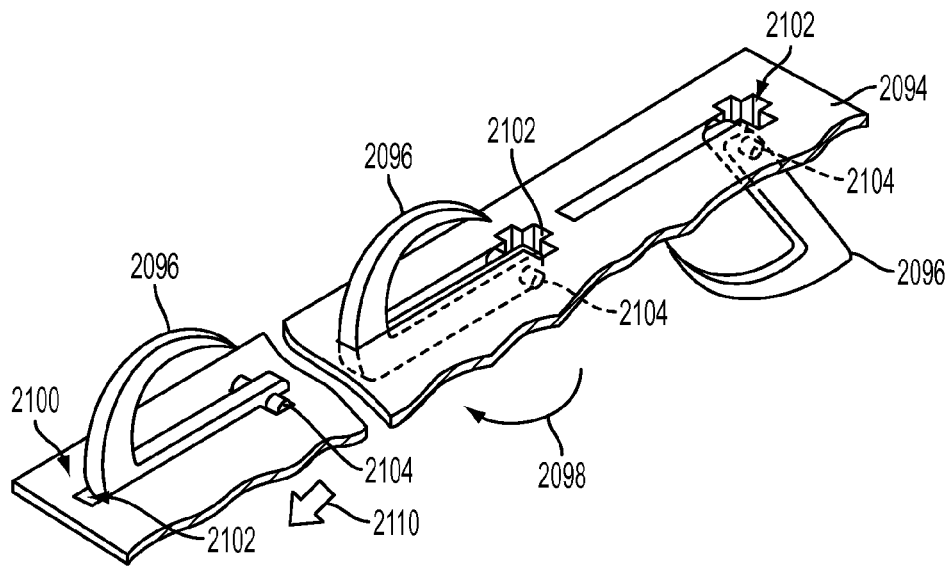
FIG. 22 is a perspective view of another embodiment of a cartridge including a separation feature adjacent to fasteners ejectable from the cartridge and each disposed within a pocket formed in the cartridge.
Figure 23:
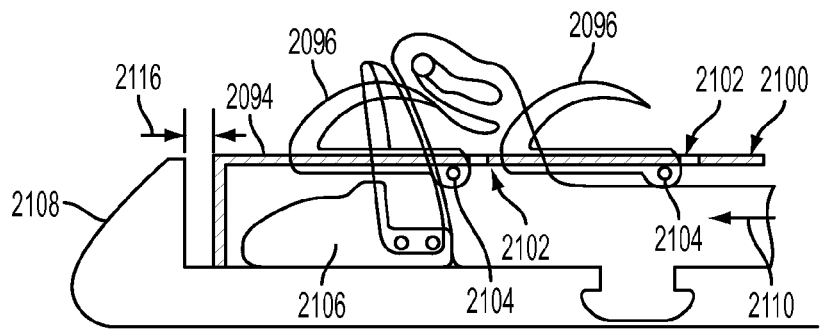
FIG. 23 is a side cross-sectional view of the separation feature of FIG. 22 within a bottom jaw of an end effector, the end effector being in a closed position.

The retainer plate 2094 can be configured to move relative to the fasteners 2096 and to the bottom jaw 2108 to facilitate ejection of the fasteners 2096 from the cartridge 2092. This movement can allow the fasteners 2096 to pass through the openings 2102 by aligning the retention pins 2104 with the opening's second slot. By way of example, a right-most one of the fasteners 2096 in FIG. 22 is shown in a stowed position within the cartridge 2092 below the tissue-engaging surface 2100 prior to the sled's engagement therewith. The middle fastener 2096 in FIG. 22 shows the fastener 2096 moved from the right-most fastener's position, the fastener 2096 having been engaged by the sled 2106 as shown in FIG. 23 to move the fastener 2096 through the opening 2102, e.g., through the first slot thereof, by rotation 2098 thereof. The retention pin 2104 is not aligned with the opening's second slot and is located under the tissue-engaging surface 2100. The left-most fastener 2096 in FIG. 22 shows the fastener 2096 released from the cartridge 2092 after the retention plate 2094 has moved relative to the fasteners 2096 and the bottom jaw 2092.

Figure 24:
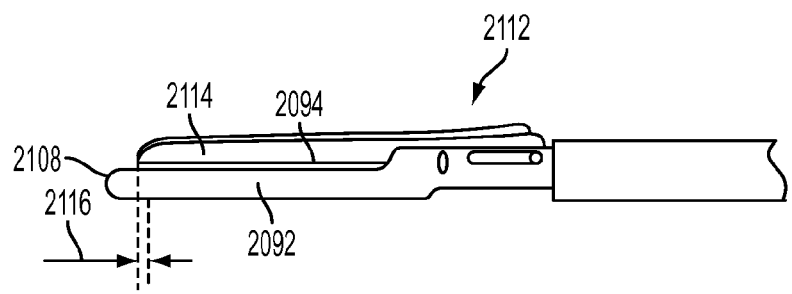
FIG. 24 is a side view of the end effector of FIG. 23.
Figure 25:
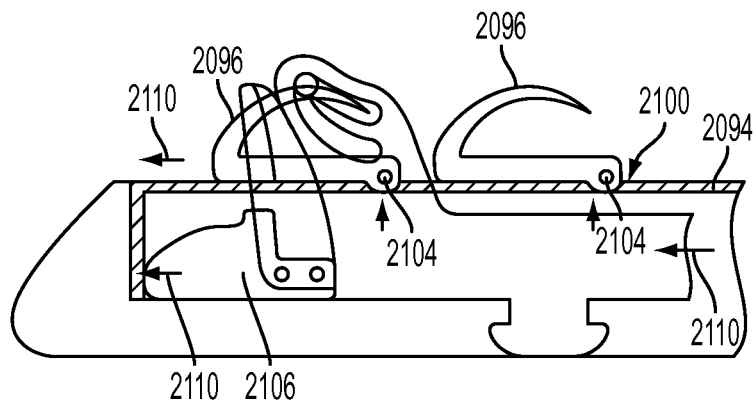
FIG. 25 is a side cross-sectional view of the separation feature of FIG. 23 within the bottom jaw of the end effector, the end effector being in an open position.
Figure 26:
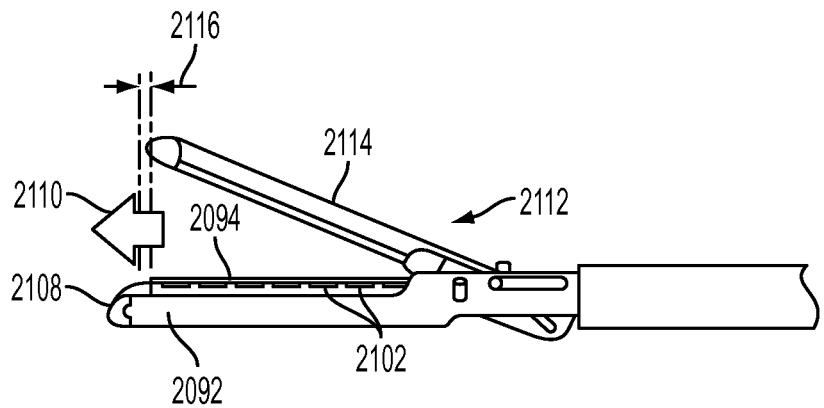
FIG. 26 is a side view of the end effector of FIG. 25.

The retention plate 2094 can be configured to move relative to the fasteners 2096 and the bottom jaw 2092 in response to an end effector 2112 that includes the bottom jaw 2092 and an upper jaw 2114 moving from a closed position, shown in FIG. 23 and FIG. 24, to an open position, shown in FIG. 25 and FIG. 26. As shown in FIG. 23, FIG. 24, FIG. 25, and FIG. 26, the retention plate 2094 can be configured to move distally in response to the opening of the end effector 2112, thereby causing the openings 2102 to align with the fastener 2096 such that the retention pins 2104 can pass therethrough, e.g., pass through the opening's second slots. The fasteners 2096 can thus be configured to all be released from the cartridge 2092 substantially simultaneously in response to the movement of the retention plate 2094. As shown in FIG. 23, FIG. 24, FIG. 25, and FIG. 26 illustrate that the retention plate 2094 can move a distance 2116 in the distal direction 2110 in response to the end effector 2112 opening.

FIG. 27, FIG. 28, FIG. 29, FIG. 30, FIG. 31, and FIG. 32 illustrate another embodiment of a cartridge 2118 that includes a separation feature 2120 that can be configured to facilitate separation of one of a plurality of fasteners 2122 disposed within the cartridge 2118. In this illustrated embodiment, the fasteners 2122 can be disposed within the cartridge 2118 as discrete elements not attached to a carrier.

The separation feature 2120 in this illustrated embodiment includes at least one tab. In general, each of the at least one tabs 2120 can be configured to retain one of the fasteners 2122 within the cartridge 2118 until a sled 2124 engages the fastener 2122 and urges the fastener 2122 upward, e.g., toward an anvil (not shown). The at least one tab 2120 can have a variety of sizes, shapes, and configurations. As in this illustrated embodiment, the at least one tab 2120 can include opposed tabs, one proximal tab and one distal tab. The cartridge 2118 can include a plurality of openings 2126 formed in a tissue-engaging surface 2128 thereof, with one of the separation features 2120 being adjacent to each one of the openings 2126, e.g., with each of the openings 2126 having associated therewith one proximal tab and one distal tab. Similar to the openings 2102 of FIG. 22, each of the openings 2126 can include a first slot extending in a proximal-distal direction and a second slot extending laterally and substantially perpendicular to the first slot such that the opening 2126 can have a "T" shape or a cross shape. The separation feature 2120 can be located at the second slot, as in this illustrated embodiment.

Figure 27:
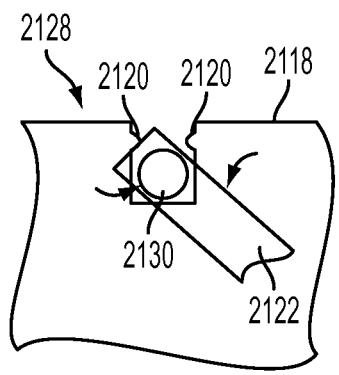
FIG. 27 is a side view of another embodiment of a cartridge including a separation feature adjacent to a fastener ejectable from the cartridge and disposed in a first position within a pocket formed in the cartridge.
Figure 28:
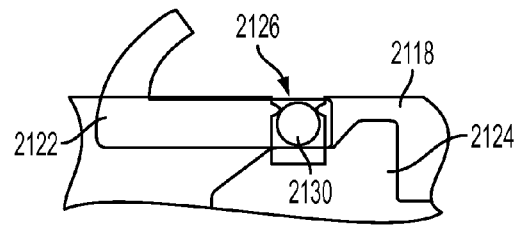
FIG. 28 is a side view of the separation feature and fastener of FIG. 27 with a sled engaging the fastener and with the fastener moved to a second position from the first position.
Figure 29:
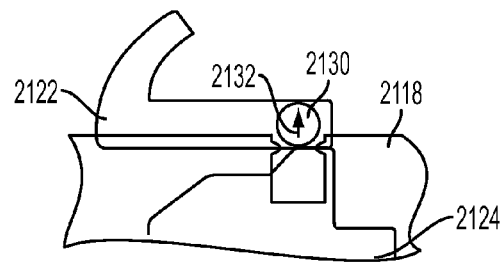
FIG. 29 is a side view of the separation feature and fastener of FIG. 28 with the sled engaging the fastener and with the fastener moved to a third position from the second position.
Figure 30:
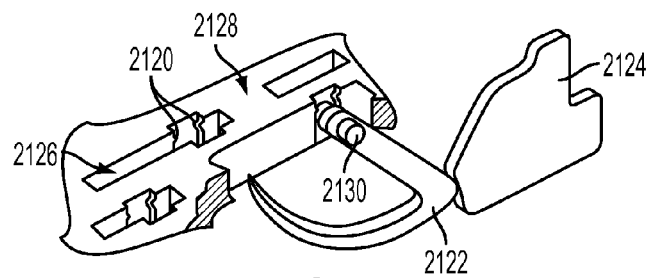
FIG. 30 is a perspective view of the fastener of FIG. 27 engaged with the sled of FIG. 28.
Figure 31:
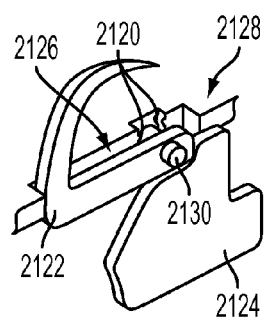
FIG. 31 is a perspective view of the fastener and sled of FIG. 28.
Figure 32:
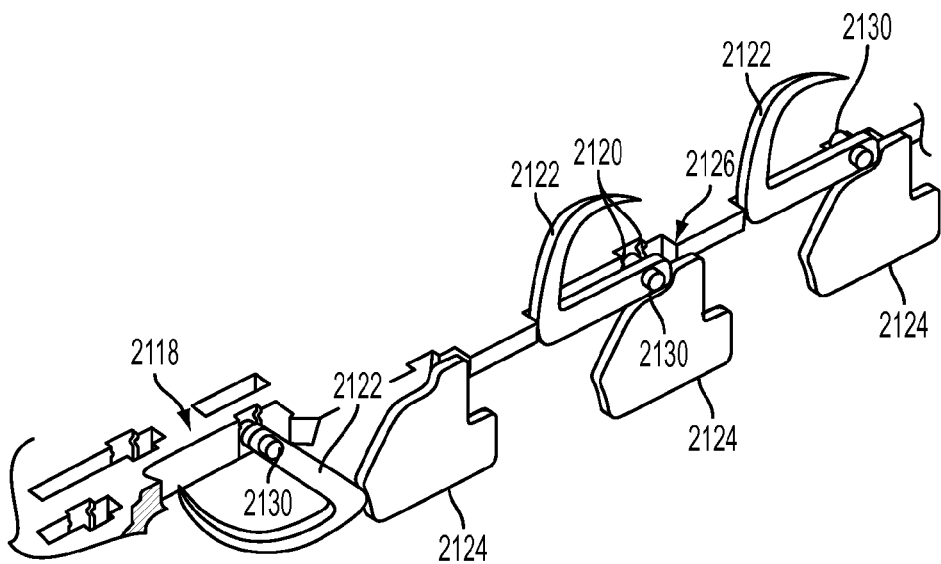
FIG. 32 is a perspective view from left to right of the fastener and sled of FIG. 30, the fastener and sled of FIG. 31, and the fastener and sled of FIG. 29.

Each of the fasteners 2122 can include a retention pin 2130. The retention pin 2130 and the at least one tab 2120 can be configured to cooperate to retain the fastener 2122 within the cartridge 2118 pre-deployment, as shown in FIG. 27, FIG. 30, and FIG. 32 (the left-most fastener 2122). In response to the sled 2124 engaging the fastener 2122, e.g., by translating distally through the cartridge 2118, the sled 2124 can cause the fastener 2122 to rotate, as shown in FIG. 28, FIG. 31, and FIG. 32 (the middle fastener 2122). The sled's continued distal advancement can, as shown in FIG. 29 and FIG. 32 (the right-most fastener 2122), cause the fastener 2122 to be pushed over the at least one tab 2120 and thereby be released from the cartridge 2118. The sled 2124 can thus be configured to provide enough of an upward force 2132, shown in FIG. 29, to push the fastener's retention pin 2130 past the at least one tab 2120. The fasteners 2122 can thus be released sequentially from the cartridge 2118 as the sled 2124 engages and pushes each of the fasteners 2122.

Figure 33:
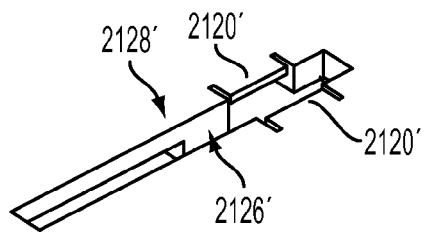
FIG. 33 is a perspective view of another embodiment of a cartridge including a separation feature.

FIG. 33 illustrates an alternate embodiment of a separation feature 2120' in the form of at least one tab that can be configured and used similar to the at least one tab 2120 of FIG. 27. In this illustrated embodiment, the at least one tab 2120' includes first and second tabs positioned on lateral sides of an opening 2126' formed in a tissue-engaging surface 2128' of a cartridge. Similar to the openings 2126 of FIG. 27, each of the openings 2126' can include a first slot extending in a proximal-distal direction and a second slot extending laterally and substantially perpendicular to the first slot such that the opening 2126' can have a "T" shape or a cross shape, and the separation feature 2120' can be extend into the second slot.

Figure 34:
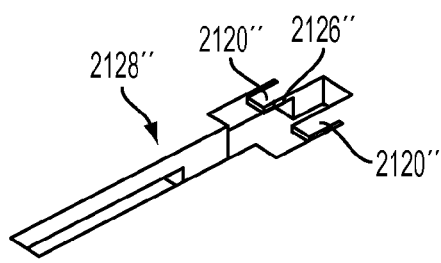
FIG. 34 is a perspective view of yet another embodiment of a cartridge including a separation feature.
Figure 35:
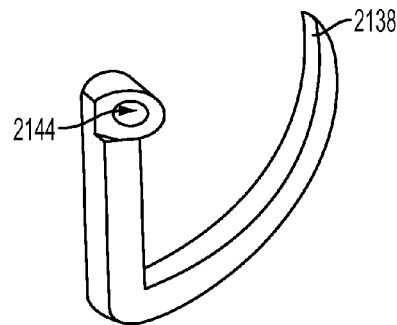
FIG. 35 is a perspective view of one embodiment of a fastener that includes a camming surface.
Figure 36:
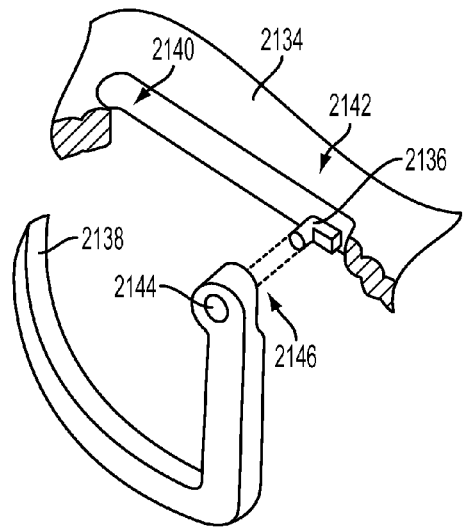
FIG. 36 is a perspective view of the fastener of FIG. 35 and another embodiment of a cartridge including a separation feature.

FIG. 34 illustrates another alternate embodiment of a separation feature 2120" in the form of at least one tab that can be configured and used similar to the at least one tab 2120 of FIG. 27. In this illustrated embodiment, the at least one tab 2120" includes first and second tabs positioned on a proximal side of an opening 2126" formed in a tissue-engaging surface 2128" of a cartridge. Similar to the openings 2126 of FIG. 27, each of the openings 2126" can include a first slot extending in a proximal-distal direction and a second slot extending laterally and substantially perpendicular to the first slot such that the opening 2126" can have a "T" shape or a cross shape, and the separation feature 2120" can extend into the second slot.

FIG. 35, FIG. 36, FIG. 37, FIG. 38, and FIG. 39 illustrate another embodiment of a cartridge 2134 that includes a separation feature 2136 that can be configured to facilitate separation of one of a plurality of fasteners 2138 disposed within the cartridge 2134. In general, each one of the separation features 2136 can be configured to cooperate with one of the fasteners 2138 to cause the fastener 2138 to move laterally relative to the separation feature 2136, e.g., relative to the cartridge 2134, to facilitate firing of the fastener 2138 through one of a plurality of openings 2140 formed in the cartridge 2134. In this illustrated embodiment, the fasteners 2138 can be disposed within the cartridge 2134 as discrete elements not attached to a carrier.

Figure 37:
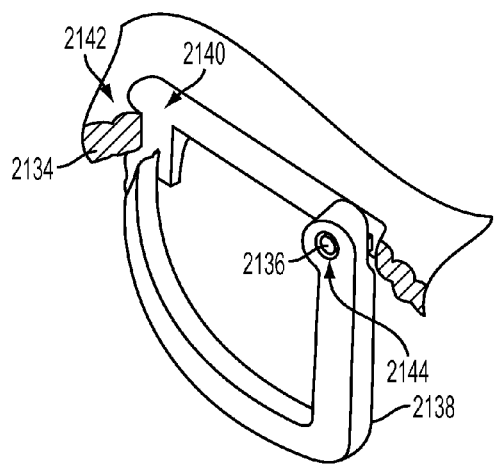
FIG. 37 is a perspective view of the fastener and cartridge of FIG. 36 with the fastener removably coupled to the separation feature and in a first position.
Figure 38:
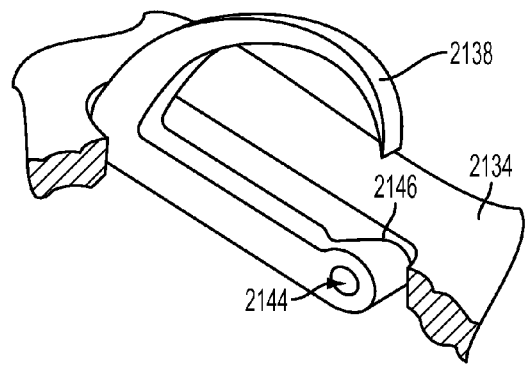
FIG. 38 is a perspective view of the fastener and cartridge of FIG. 37 with the fastener moved to a second position from the first position.
Figure 39:
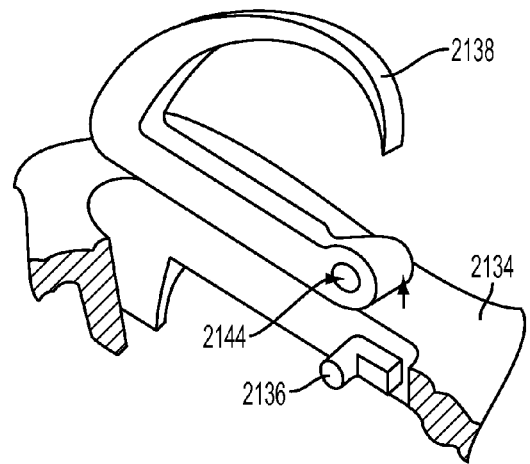
FIG. 39 is a perspective view of the fastener and cartridge of FIG. 38 with the fastener moved to a third position from the second position.
Figure 40:
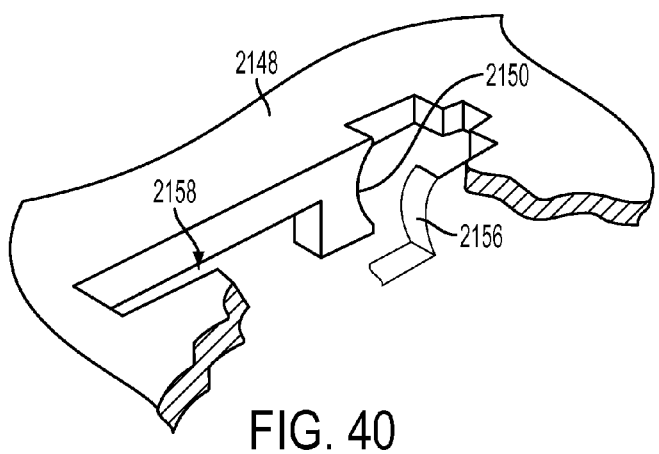
FIG. 40 is a perspective view of another embodiment of a fastener that includes a camming surface and another embodiment of a cartridge including a separation feature.
Figure 41:
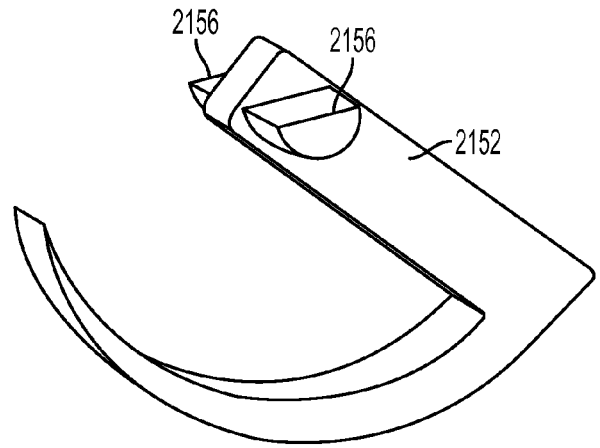
FIG. 41 is a perspective view of the fastener of FIG. 40.

The separation feature 2136 in this illustrated embodiment includes a post configured to releasably engage the fastener 2138. The post 2136 can have a variety of sizes, shapes, and configurations. As in this illustrated embodiment, the post 2136 can be located adjacent the opening 2140 and can extend laterally from an internal surface of the cartridge 2134 below a tissue-engaging surface 2142 of the cartridge 2134. The post 2136 can be configured to be seated in a hole 2144 formed in its associated fastener 2136 when the fastener 2136 is disposed within the cartridge 2134, as shown in FIG. 37. The fastener 2136 can include a cam surface 2146 adjacent the hole 2144 that can be configured to slidably engage the post 2136 when the fastener 2138 is being rotated out of the opening 2140 in response to an urging force from a sled (not shown) translating through the cartridge 2134, as shown in FIG. 38. A longitudinal axis of the post 2136 can define an axis of the fastener's rotation. The cam surface's engagement with the post 2136 can cause the fastener 2138 to move laterally relative to the post 2136 and a remainder of the cartridge 2134. In other words, the cam surface 2146 can cause the fastener 2138 to be cammed laterally. The lateral movement of the fastener 2136 can cause the post 2136 to move out of the hole 2144, thereby allowing the fastener 2136 to exit the opening 2140, as shown in FIG. 39. The fasteners 2138 can thus be released sequentially from the cartridge 2134 as the sled engages and pushes each of the fasteners 2138.

FIG. 40, FIG. 41, FIG. 42, FIG. 43, FIG. 44, and FIG. 45 illustrate another embodiment of a cartridge 2148 that includes a separation feature 2150 that can be configured to facilitate separation of one of a plurality of fasteners 2152 disposed within the cartridge 2148. In this illustrated embodiment, the fasteners 2152 can be disposed within the cartridge 2148 as discrete elements not attached to a carrier. In general, each one of the separation features 2150 can be configured to cooperate with a retention feature 2156 of one of the fasteners 2152 to cause the fastener 2152 to exit the cartridge 2148 through one of a plurality of openings 2158 formed in the cartridge 2148.

Figure 42:
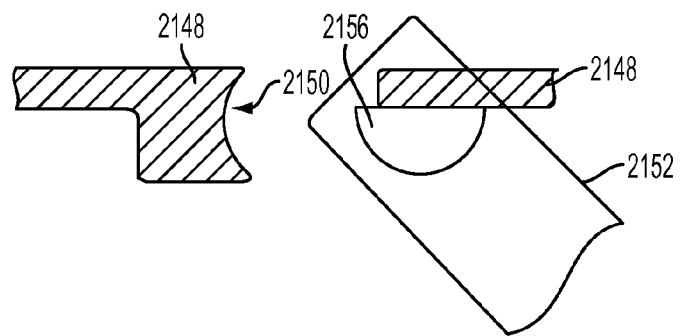
FIG. 42 is a side, partially cross-sectional view of the fastener and cartridge of FIG. 40, the fastener being in a first position.
Figure 43:
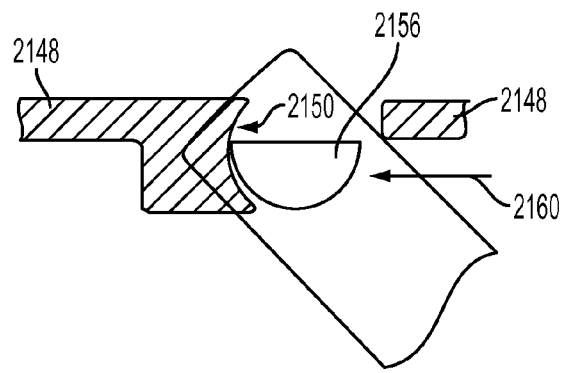
FIG. 43 is a perspective view of the fastener and cartridge of FIG. 42 with the fastener moved to a second position from the first position.
Figure 44:
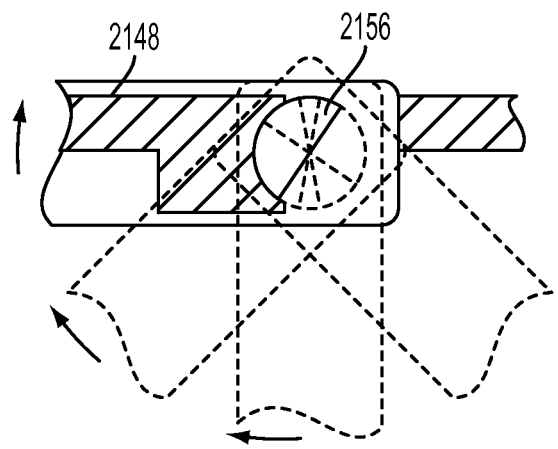
FIG. 44 is a perspective view of the fastener and cartridge of FIG. 43 with the fastener moved to a third position from the second position.

The separation feature 2150 in this illustrated embodiment includes a cam surface 2154 configured to engage the corresponding retention feature 2156, e.g., a cam, of the fastener 2152. The cam surface 2154 and the cam 2156 can have a variety of sizes, shapes, and configurations. As in this illustrated embodiment, the cam surface 2154 can have a curved shape, and the cam 2156 can have a corresponding curved shape configured to slidably engage the cam surface 2154, as shown in FIG. 43 and FIG. 44. In addition to its curved surface, the cam 2156 can have a substantially flat surface. The cam's substantially flat surface can be configured to engage an inner surface of the cartridge 2148 when the fastener 2152 is disposed within its pocket formed in the cartridge 2148, as shown in FIG. 42. The engagement of the cam's substantially flat surface and the cartridge's inner surface can facilitate retention of the fastener 2152 within the cartridge 2148 until a sled (not shown) translates through the cartridge 2148 to rotate the fastener 2152 and thereby urge the fastener 2152 out of the opening 2158. In this illustrated embodiment, the cam 2156 includes two pins each having a half moon shape and each extending laterally from the fastener 2152 adjacent a proximal end of the fastener 2152, but the cam 2156 can, as mentioned above, have other shapes and configurations. For example, a fastener can include only one pin extending laterally from one side of the fastener, can include only one pin extending through the fastener to extend laterally from opposed sides thereof, etc.

Figure 45:
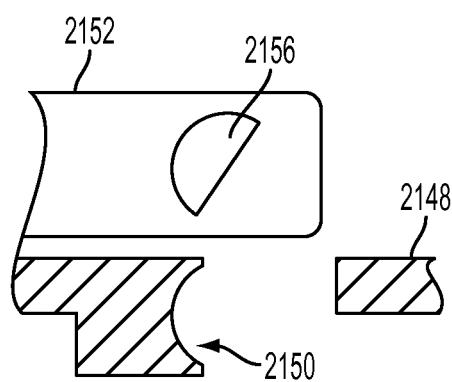
FIG. 45 is a perspective view of the fastener and cartridge of FIG. 43 with the fastener moved to a fourth position from the third position.

As shown in FIG. 42, the fastener 2152 can be disposed within the cartridge 2148 in a first position with the cam 2156, e.g., the substantially flat surface thereof, engaging the inner surface of the cartridge 2148. When the sled translates in a distal direction 2160 through the cartridge 2148 and engages the fastener 2152, the fastener 2152 can be pushed in the distal direction 2160 such that the cam 2156 disengages from the inner surface of the cartridge 2156 and contacts the cam surface 2150, as shown in FIG. 43. As shown in FIG. 44, continued distal movement of the sled can cause the cam 2156, e.g., the curved surface thereof, to slidably engage the cartridge's cam surface 2150, thereby causing the fastener 2152 to rotate. The fastener 2152 can then rotate out of the opening 2158, as shown in FIG. 45.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:
1. A surgical fastening device for treating tissue, comprising:
    an elongate shaft; an end effector coupled to a distal end of the elongate shaft, the end effector including a jaw and an anvil pivotally connected to the jaw, the jaw and the anvil being configured to engage tissue therebetween;
    a plurality of fasteners disposed within the jaw and frangibly coupled to a carrier;

a sled configured to advance distally through the jaw to cause each of the plurality of fasteners to rotate into tissue engaged between the jaw and the anvil; and a shearing element slidably moveable within the jaw to shear each fastener from the carrier, the shearing element being configured to shear the fasteners from the carrier after the fasteners are driven into tissue by the sled, the shearing element being pivotable between a first inactive position and a second active position, and the shearing element shearing the fasteners during the second active position.

2. The device of claim 1, wherein the shearing element is positioned proximal of the sled.

3. The device of claim 1, wherein the shearing element includes a plurality of upright wedges configured to shear the fasteners from the carrier.

4. The device of claim 1, wherein the shearing element is coupled to a distal end of the sled.

5. The device of claim 4, further comprising an I-beam positioned proximal of the shearing element and configured to be slidably received within the anvil and the jaw.

6. The device of claim 1, wherein the sled include a plurality of wedges configured to contact and drive the fasteners into tissue, and a knife for cutting tissue engaged between the jaw and the anvil, and wherein the shearing element is positioned proximal of the wedges and the knife.

7. The device of claim 1, wherein the shearing element is configured to shear the fasteners from the carrier during proximal movement of the shearing element through the jaw.

8. The device of claim 1, wherein the shearing element is separate from the sled.

9. A surgical stapling device, comprising:

an end effector having first and second jaws pivotally coupled to one another and configured to engage tissue therebetween;

a plurality of plastically deformable staples frangibly formed on a carrier and disposed within the first jaw, the staples being configured to be rotatably deployed into tissue engaged between the jaws;

a wedge configured to slidably advance through the first jaw to rotatably drive the staples into tissue; and a shearing element configured to shear the staples from the carrier after the staples are rotatably deployed into the tissue by the wedge, the shearing element being pivotable between a first inactive position and a second active position, the shearing element shearing the staples during the second active position.

10. The device of claim 9, wherein the shearing element is positioned proximal of the wedge.

11. The device of claim 9, wherein the wedge includes a plurality of upright flanges configured to rotatably drive the staples into tissue, and the shearing element includes a plurality of upright flanges configured to shear the staples from the carrier.

12. The device of claim 9, wherein the wedge includes a knife for cutting tissue engaged between the first and second jaws, and wherein the shearing element is positioned proximal of the knife.

13. The device of claim 9, wherein the shearing element is configured to shear the staples from the carrier during proximal movement of the shearing element through the first jaw.

* * * * *